US008524496B2

(12) United States Patent
Meiron et al.

(10) Patent No.: US 8,524,496 B2
(45) Date of Patent: Sep. 3, 2013

(54) ADHERENT CELLS FROM PLACENTA TISSUE AND USE THEREOF IN THERAPY

(75) Inventors: Moran Meiron, Zikhron-Yaakov (IL); Amir Toren, Zikhron-Yaakov (IL); Rachel Ofir, Mitzpe Adi (IL); Nirit Drori-Carmi, Doar-Na Hof HaCarmel (IL)

(73) Assignee: Pluristem Ltd., Haifa (IL)

( * ) Notice: Subject to any disclaimer, the term of this patent is extended or adjusted under 35 U.S.C. 154(b) by 0 days.

(21) Appl. No.: 13/061,538

(22) PCT Filed: Sep. 1, 2009

(86) PCT No.: PCT/IL2009/000846
§ 371 (c)(1),
(2), (4) Date: Jul. 8, 2011

(87) PCT Pub. No.: WO2010/026575
PCT Pub. Date: Mar. 11, 2010

(65) Prior Publication Data
US 2011/0256159 A1    Oct. 20, 2011

Related U.S. Application Data

(60) Provisional application No. 61/136,375, filed on Sep. 2, 2008, provisional application No. 61/202,050, filed on Jan. 23, 2009.

(51) Int. Cl.
*C12M 3/00* (2006.01)
*A01N 1/02* (2006.01)

(52) U.S. Cl.
USPC .......................................... 435/395; 435/375

(58) Field of Classification Search
None
See application file for complete search history.

(56) References Cited

U.S. PATENT DOCUMENTS

2008/0131934 A1* 6/2008 Crowley et al. .............. 435/70.3
2011/0129447 A1* 6/2011 Meretzki et al. ............. 424/93.7

FOREIGN PATENT DOCUMENTS

WO    WO2007/108003    *    9/2007

OTHER PUBLICATIONS

Bartholomew et al., 2002, Experimental Hematology, 30: 42-48.*
Halleux et al., 2001, J. Musculoskel Neuron Interact, 2: 71-76.*
Life Technologies, Technical Resources-Media Formulations [online], 2012 [retrieved on Sep. 14, 2012]. Retrieved from the Internet< URL: http://www.invitrogen.com/site/us/en/home/support/Product-Technical-Resources/media_formulation.53.html>, pp. 1-2.*
DMEM product sheet, per Biological Industries.*
Soncini et al. "Isolation and characterization of mesenchymal cells from human fetal membranes." Journal of Tissue Engineering and Regenerative Medicine Jul.-Aug. 2007; 1: 296-305.*

* cited by examiner

*Primary Examiner* — Joanne Hama
*Assistant Examiner* — Titilayo Moloye
(74) *Attorney, Agent, or Firm* — Finnegan, Henderson, Farabow, Garrett & Dunner LLP

(57) ABSTRACT

A method of culturing adherent cells from a placenta or adipose tissue is disclosed. The method comprising culturing the adherent cells from the placenta or adipose tissue under 3 dimensional (3D) culturing conditions which allow cell expansion, the conditions comprising perfusion.

4 Claims, 14 Drawing Sheets

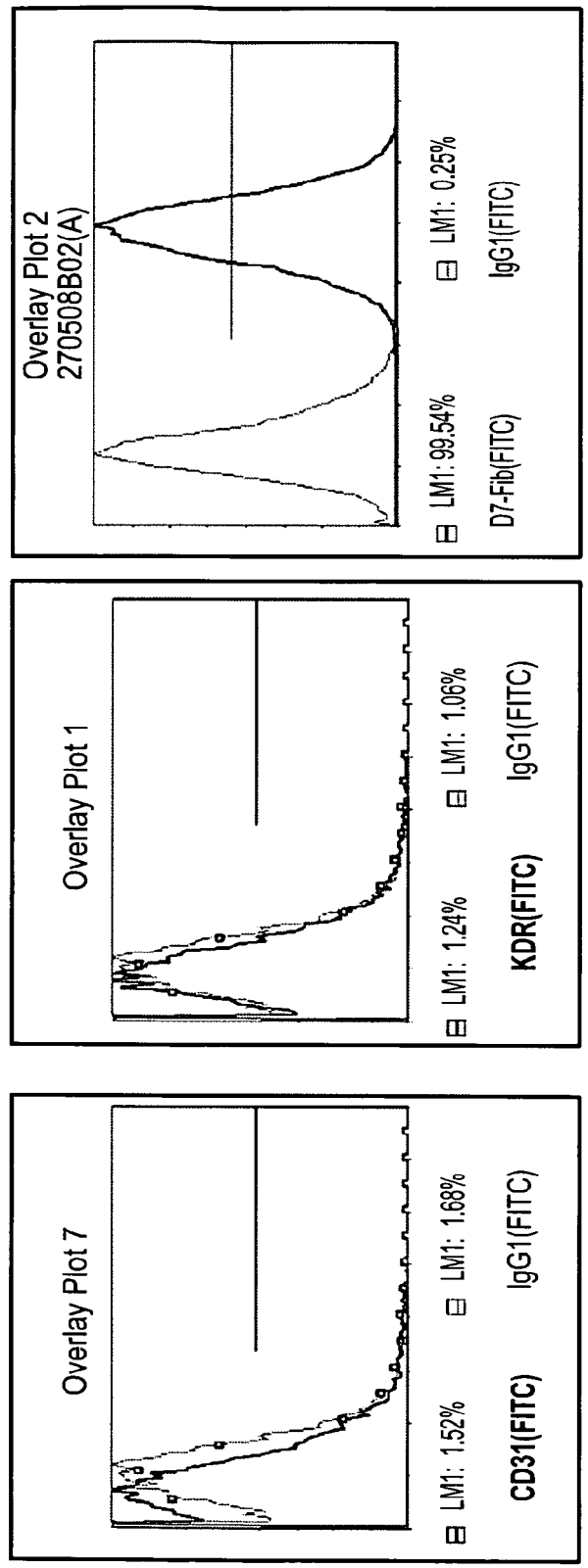

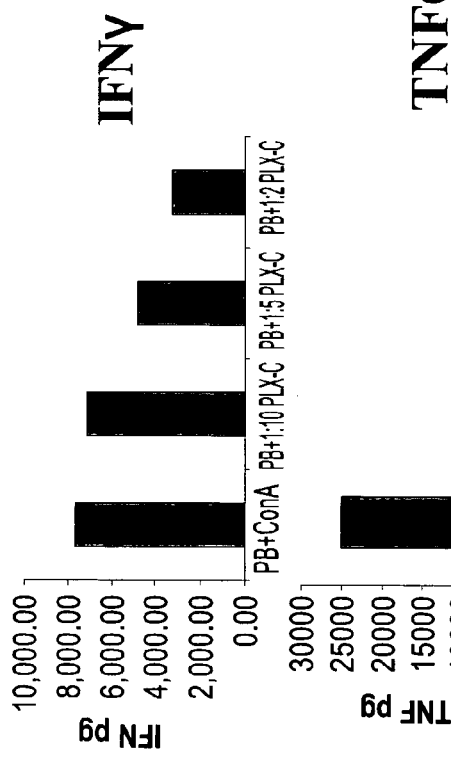
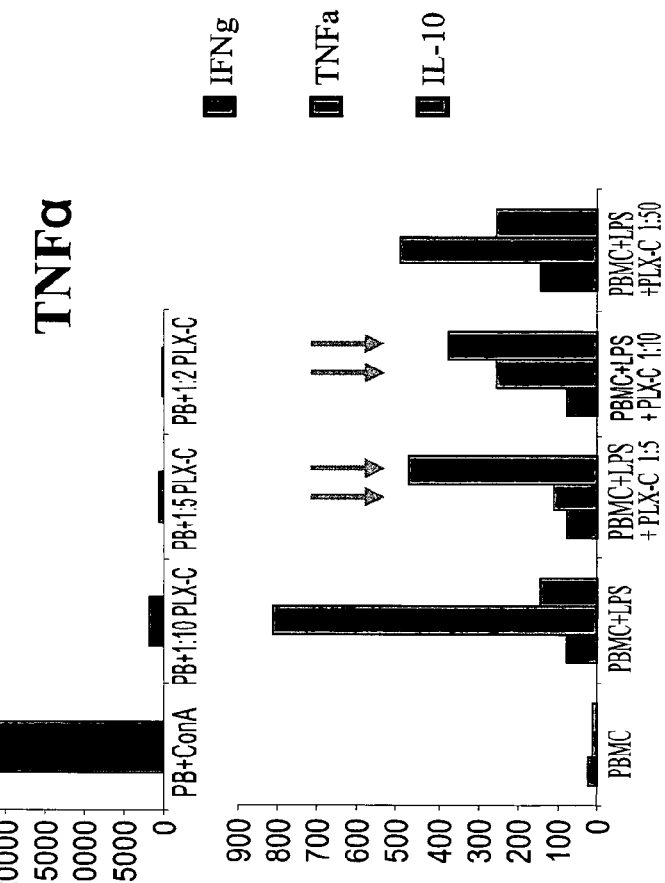
FIG. 7A
FIG. 7B
FIG. 7C

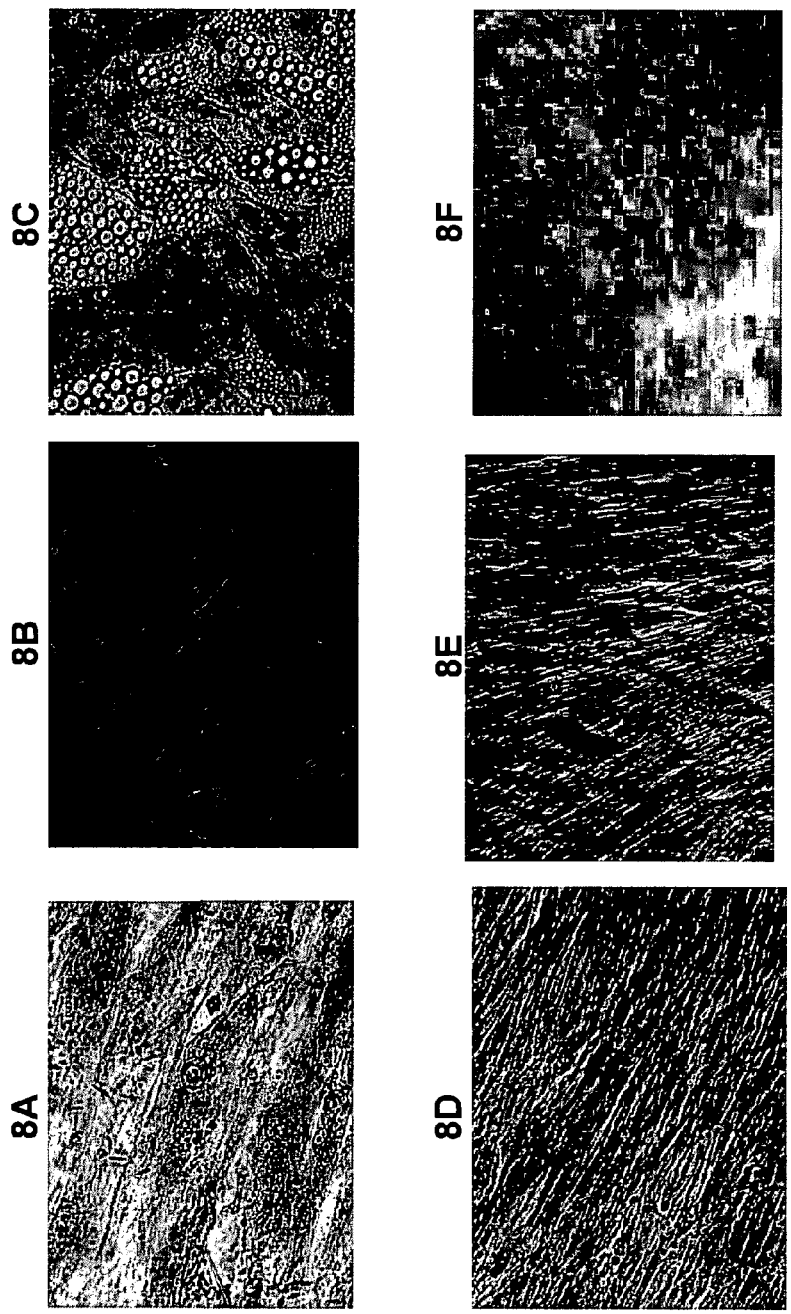

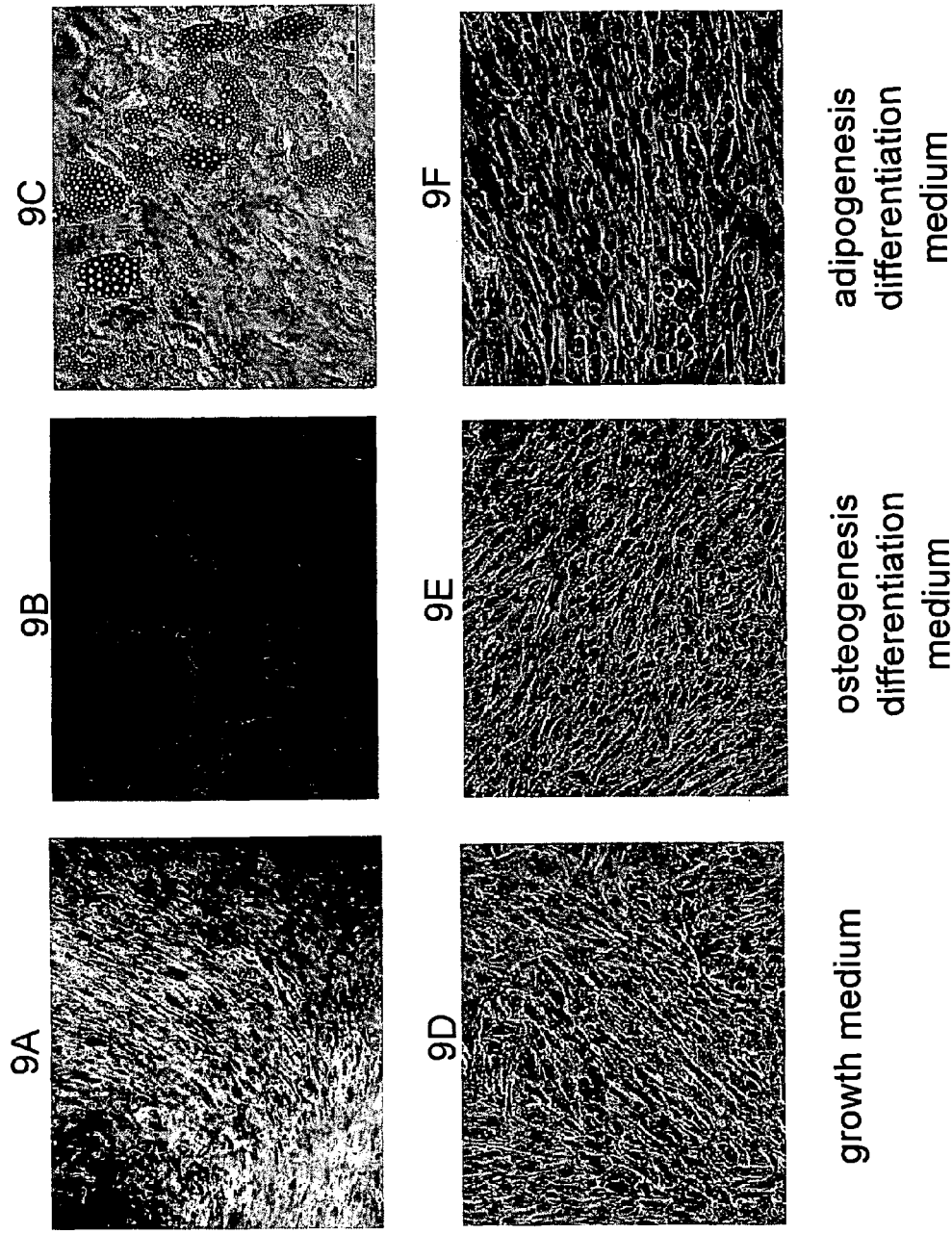
FIGs. 9A-F

ADHERENT CELLS FROM PLACENTA TISSUE AND USE THEREOF IN THERAPY

RELATED APPLICATIONS

This application is the National Phase of International Application No. PCT/IL2009/000846, filed Sep. 1, 2009, and claims benefit of U.S. Provisional Patent Application No 61/202,050, filed Jan. 23, 2009 and U.S. Provisional Patent Application No. 61/136,375, filed Sep. 2, 2008.

The contents of all of the above documents are incorporated by reference as if fully set forth herein.

FIELD AND BACKGROUND OF THE INVENTION

The present invention, in some embodiments thereof, relates to adherent cells of placenta tissue and, more particularly, but not exclusively, to methods of culturing same and using same for treatment.

In recent years, considerable activity has focused on the therapeutic potential of mesenchymal stromal cells (MSCs) for various medical applications including tissue repair of damaged organs such as the brain, heart, bone and liver and in support of bone marrow transplantations (BMT). MSCs, a heterogeneous population of cells obtained from e.g. bone marrow, adipose tissue, placenta, and blood, is capable of differentiating into different types of cells (e.g. reticular endothelial cells, fibroblasts, adipocytes, osteogenic precursor cells) depending upon influences from various bioactive factors. Accordingly, MSCs have been widely studied in regenerative medicine as the foundation to build new tissues such as bone, cartilage and fat for the repair of injury or replacement of pathologic tissues and as treatment for genetic and acquired diseases [Fibbe and Noort, Ann N Y Acad Sci (2003) 996: 235-44; Horwitz et al., Cytotherapy (2005) 7(5): 393-5; Zimmet and Hare, Basic Res Cardiol (2005) 100(6): 471-81]. Furthermore, the multipotent ability of MSCs, their easy isolation and culture, as well as their high ex vivo expansion potential make them an attractive therapeutic tool [Fibbe and Noort, supra; Minguell et al. Exp Biol Med (Maywood) (2001) 226(6): 507-20].

An emerging body of data indicates that MSCs escape recognition of alloreactive cells and are considered to be immune privileged [Le Blanc et al., Exp Hematol (2003) 31(10): 890-6]. Having low immunogenicity, MSCs are not rejected by the patient's immune system and therefore are considered not to require HLA matching.

Placental derived MSCs exhibit many markers common to MSCs isolated from other tissues, e.g. CD105, CD73, CD90 and CD29, and the lack of expression of hematopoietic, endothelial and trophoblastic-specific cell markers. Adipogenic, osteogenic, and neurogenic differentiation have been achieved after culturing placental derived MSCs under appropriate conditions [Yen et al., Stem Cells (2005) 23(1): 3-9]. Furthermore, MSCs isolated from placenta and cultured in vitro have been demonstrated to be immune privileged in a similar fashion as MSCs [Li et al., Cell Res (2005) 15(7): 539-47]. Thus, the placenta provides an ethically non-controversial and easily accessible source of MSCs for experimental and clinical applications [Zhang et al., Exp Hematol (2004) 32(7): 657-64]. In addition, the present inventors have previously devised three dimensional (3D) culturing conditions suitable for expansion of placental derived MSCs (WO/2007/108003).

SUMMARY OF THE INVENTION

According to an aspect of some embodiments of the present invention there is provided a method of culturing adherent cells from a placenta or adipose tissue, the method comprising culturing the adherent cells from the placenta or adipose tissue under 3 dimensional (3D) culturing conditions which allow cell expansion, the conditions comprising perfusion.

According to an aspect of some embodiments of the present invention there is provided a population of cells generated according to the above method.

According to an aspect of some embodiments of the present invention there is provided a population of cells comprising a gene expression profile essentially as described herein.

According to an aspect of some embodiments of the present invention there is provided a use of the population of cells, for the manufacture of a medicament identified for treating a condition which can benefit from cell or organ transplantation.

According to an aspect of some embodiments of the present invention there is provided a method of inducing tolerance and/or immunosuppression in a subject in need thereof, the method comprising administering to the subject a therapeutically effective amount of the adherent cells, thereby inducing tolerance and/or immunosuppression in the subject.

According to some embodiments of the invention, the perfusion is adjusted according to the glucose concentration of the culture medium.

According to some embodiments of the invention, the culture medium is maintained at a glucose concentration of about 550 mg/L. According to some embodiments of the invention, the 3D culturing conditions comprise a 3D bioreactor.

According to some embodiments of the invention, the 3D culturing conditions comprise an adherent material selected from the group consisting of glass and plastic; polyester, polypropylene, polystyrene, dextran and collagen.

According to some embodiments of the invention, the 3D culturing conditions are effected for at least 3 days.

According to some embodiments of the invention, culturing of the cells is effected until at least 10% of the cells are proliferating.

According to some embodiments of the invention, at least 10% of the adherent cells are at a proliferative phase.

According to some embodiments of the invention, the adherent cells are capable of suppressing an immune reaction.

According to some embodiments of the invention, the adherent cells comprise a positive marker expression selected from the group consisting of CD73, CD90, CD29, CD105 and D7-fib.

According to some embodiments of the invention, the adherent cells comprise a negative marker expression selected from the group consisting of CD11b, CD34, HLA-DR, CD14, CD19, CD45, CD31, CD200 and KDR.

According to some embodiments of the invention, the adherent cells comprise a gene expression profile essentially as described herein.

According to some embodiments of the invention, the adherent cells are less committed to an osteogenic lineage as compared to adherent cells from bone marrow grown and allowed to differentiate under the same conditions.

According to some embodiments of the invention, the adherent cells are less committed to an adipogenic lineage as compared to adherent cells from bone marrow grown and allowed to differentiate under the same conditions.

According to some embodiments of the invention, the condition is selected from the group consisting of ischemia, peripheral arterial disease (PAD), critical limb ischemia (CLI), lower extremity ischemia, ischemic vascular disease, vascular disease of the kidney, ischemic heart disease, myocardial ischemia, coronary artery disease (CAD), atherosclerotic cardiovascular disease, left main coronary artery disease, arterial occlusive disease, peripheral ischemia, peripheral vascular disease, arteriosclerosis, ischemic brain disease, stroke, cerebral ischemia, cerebro vascular disease, retinopathy, retinal repair, remodeling disorder, von Hippel-Lindau syndrome, hereditary hemorrhagic telengiectasiaischemic vascular disease, Buerger's disease, ischemic renal disease, ischemic placenta, reproduction associated disorders, graft-versus-host disease, solid organ transplantation, hematopoietic stem cell transplantation, diabetes, connective tissue damage, cancer, pre-cancer, bone cancer, osteosarcoma, bone metastases, bone fracture, burn wound, articular cartilage defect, wound healing, deep wound, delayed wound-healing, delayed ulcer healing, subchondral-bone cyst, osteoporosis, osteoarthritis, degenerated bone, cartilage damage, articular cartilage defect, injured tendons, autoimmune disease, metabolic disorders, psoriasis, neuropathic pain, peripheral nerve injury, support of kidney transplantation and inflammatory disease.

According to some embodiments of the invention, the condition is selected from the group consisting of inflammatory bowel disease (IBD) and Crohn's disease.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 4A-D depict expression of fibroblast-typical markers but not expression of endothelial typical markers on PLX-C. FIG. 4A depicts negative expression of the endothelial marker CD31; FIG. 4B depicts negative expression of the endothelial marker KDR; FIG. 4C depicts positive expression of the human fibroblast marker (D7-FIB), wherein the red histograms for Isotype IgG1 (FITC) represent the negative control while the blue histograms represent the positively stained cells); and FIG. 4D depicts negative expression of the human CD200 marker (the pink histograms for Isotype IgG1 (PE) represent the negative control while the green histograms represent the positively stained cells).

FIG. 5A depicts PLX-C expression of CD80; FIG. 5B depicts PLX-C expression of CD86; FIG. 5C depicts PLX-C expression of CD40; and FIG. 5D depicts PLX-C expression of HLA-AB/C. Negative controls were prepared with relevant isotype fluorescence molecules. Of note, red histograms indicate PLX-C marker-expressing population of cells, blue histograms indicate bone marrow (BM) marker-expressing population of cells, and green histograms indicate mononuclear cell (MNC) marker expressing population of cells.

FIG. 6A depicts Mixed Lymphocyte Reaction (MLR) tests performed with $2 \times 10^5$ peripheral blood (PB) derived mononuclear cells (MNC, donor A) stimulated with equal amount of irradiated (3000 Rad) PB derived MNCs (donor B) followed by addition of increasing amounts of PLX-C cells to the cultures. Three replicates of each group were seeded in 96-well plates. Proliferation rate was measured by [$^3$H]thymidine incorporation; FIG. 6B depict peripheral blood (PB) derived MNCs stimulated with ConA (1.5 mg/ml). Increasing amounts of PLX-C cells were added to the cultures. Three replicates of each group were seeded in 96-well plates. Proliferation rate was measured by [$^3$H] thymidine incorporation.

FIGS. 7A-C depict PLX-C regulation of pro-inflammatory and anti-inflammatory cytokine secretion following co-culture with peripheral blood cells. FIGS. 7A-B depict secretion of IFNγ (FIG. 7A) and TNFα (FIG. 7B) following co-culture of human derived MNCs (isolated from peripheral blood) stimulated with ConA with PLX-C; FIG. 7C depicts secretion of IFNγ, TNFα and IL-10 following co-culture of human derived MNCs (isolated from peripheral blood) stimulated with LPS with PLX-C. Supernatants were collected and subjected to cytokines analysis using ELISA.

FIGS. 8A-F are photographs depicting growth of bone marrow and placenta cells under osteogenesis or adipogenesis differentiation conditions. Bone marrow derived cells (FIGS. 8A-C) or placenta derived cells (FIGS. 8D-F) were plated in growth medium (FIGS. 8A and 8D), osteogenesis differentiation medium (FIGS. 8B and 8E) or adipogenesis differentiation medium (FIGS. 8C and 8F) in a 24 well plate coated with vitronectin and collagen. Medium was replaced every 3-4 days. At the end of growth period cells were fixed, stained and pictured as described in detail the Examples section which follows.

FIGS. 9A-F are photographs depicting growth of bone marrow and placenta cells under modified osteogenesis or adipogenesis differentiation conditions. Bone marrow derived cells (FIGS. 9A-C) or placenta derived cells (FIGS. 9D-F) were plated in growth medium (FIGS. 9A and 9D), osteogenesis differentiation medium (FIGS. 9B and 9E) or adipogenesis differentiation medium (FIGS. 9C and 9F) in a 24 well plate coated with vitronectin and collagen. Medium was replaced every 3-4 days. At the end of growth period cells were fixed, stained and pictured as described in detail the Examples section which follows.

DESCRIPTION OF SPECIFIC EMBODIMENTS OF THE INVENTION

Figure 1:
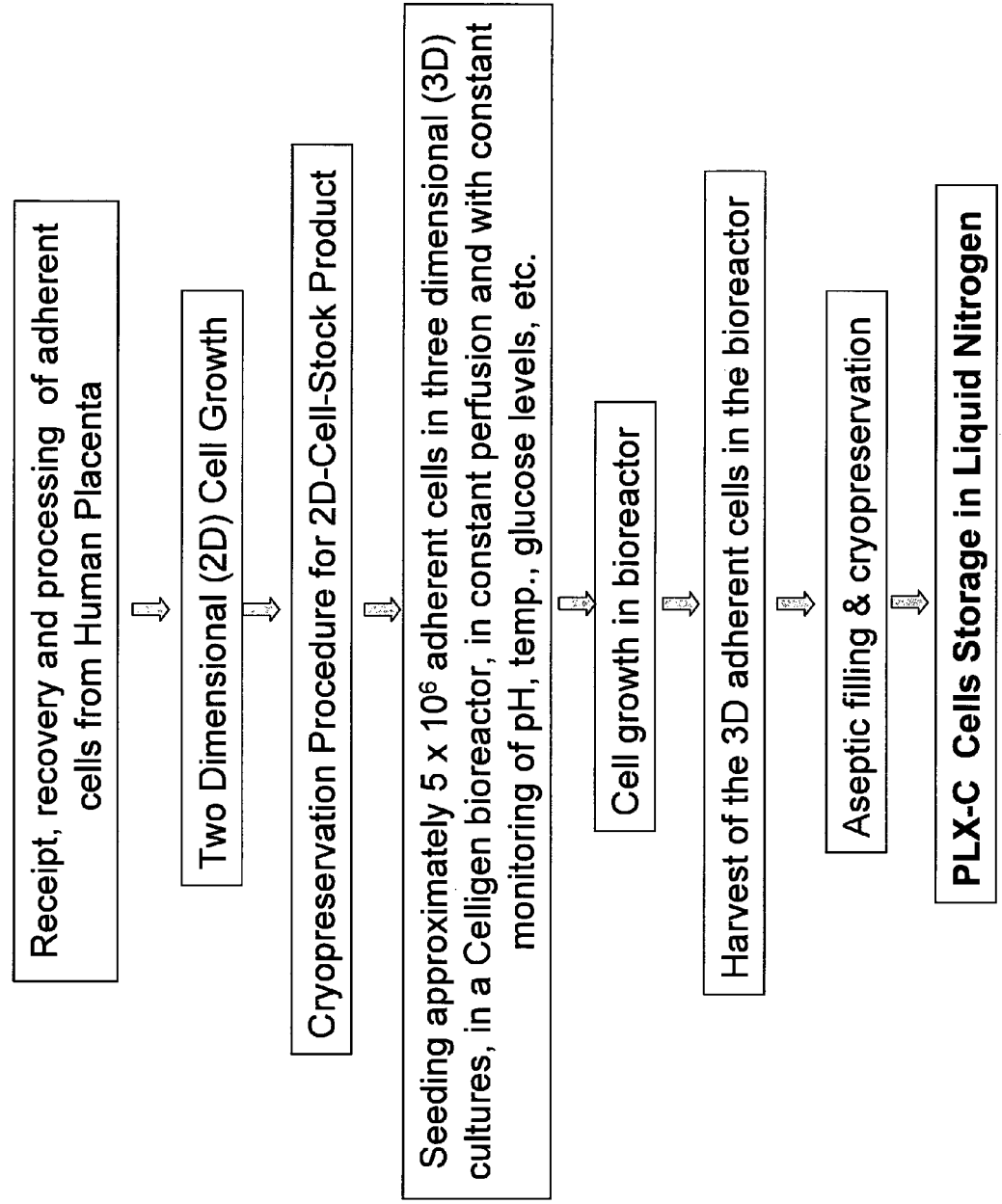
FIG. 1 is a flow chart depicting production of 3D adherent cell from placentas according to the present teachings (designated PLX-C cells).

The present invention, in some embodiments thereof, relates to adherent cells of placenta tissue and, more particularly, but not exclusively, to methods of culturing same and using same for treatment.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

While reducing the present invention to practice, the present inventors have uncovered that culturing placenta derived adherent cells under three dimensional (3D) culturing conditions, comprising perfusion, generate large amounts of adherent cells which are characterized by a distinctive gene expression profile, are capable of suppressing an immune response and are highly proliferative. Thus, these placenta adherent cells may be used for therapeutic applications.

As is illustrated herein below and in Example 1-8 of the Examples section which follows, the present inventors were able to expand placenta-derived adherent cells under 3D conditions. The 3D conditions of the present invention comprise perfusion of the cell medium within the bioreactor (see Example 2). As is shown in Example 3, the placenta adherent cells of the present invention comprise stromal stem cell properties, e.g. they express cellular markers typical of stromal stem cells, and comprise immunosuppressive properties. Furthermore, these cells are highly proliferative (28% of cells were in S and G2/M phases) and are retained in the body for a few weeks after administration (see Examples 3 and 8), suggesting these cells may be used for treatment.

In addition, in their 2D stage, the placenta derived adherent cells of the present invention did not differentiate into osteocytes (Examples 4-5) or adipocytes (Examples 6-7), in sharp contrast to bone marrow adherent cells of which a high percentage (over 50%) underwent differentiation when grown under the same conditions.

Thus, according to one aspect of the present invention there is provided a method of culturing adherent cells from a placenta or adipose tissue, the method comprising culturing the adherent cells from the placenta or adipose tissue under three dimensional (3D) culturing conditions which allow cell expansion, the conditions comprising perfusion.

As used herein the phrase "adherent cells" refers to a homogeneous or heterogeneous population of cells which are anchorage dependent, i.e., require attachment to a surface in order to grow in vitro.

As used herein the phrase "adipose tissue" refers to a connective tissue which comprises fat cells (adipocytes).

As used herein the term "placenta tissue" refers to any portion of the mammalian organ which lines the uterine wall and during pregnancy envelopes the fetus, to which it is attached by the umbilical cord. Following birth, the placenta is expelled (and is referred to as a post partum placenta). In an exemplary embodiment, placenta refers to whole placenta.

According to the present teachings, placenta or adipose tissue derived adherent cells are propagated using three dimensional (3D) culturing conditions.

As used herein the phrase "three dimensional culture" refers to a culture in which the cells are disposed to conditions which are compatible with cell growth including a scaffold which allows cell to cell contacts in three dimensions. It is well appreciated that the in situ environment of a cell in a living organism (or a tissue) is in a three dimensional architecture. Cells are surrounded by other cells. They are held in a complex network of extra cellular matrix nanoscale fibers that allows the establishment of various local microenvironments. Their extra cellular ligands mediate not only the attachment to the basal membrane but also access to a variety of vascular and lymphatic vessels. Oxygen, hormones and nutrients are ferried to cells and waste products are carried away. The conditions in the three dimensional culture of the invention are designed to mimic such an environment as is further exemplified below.

It will be appreciated that the conditions of the three-dimensional culture are such that enable expansion of the adherent cells.

As used herein the terms "expanding" and "expansion" refer to substantially differentiation-less maintenance of the cells and ultimately cell growth, i.e., increase of a cell population (e.g., at least 2 fold) without differentiation accompanying such increase. As used herein the terms "maintaining" and "maintenance" refer to substantially differentiation-less cell renewal, i.e., substantially stationary cell population without differentiation accompanying such stationarity.

As mentioned, the adherent cells of this aspect of the invention are retrieved from a placental or adipose tissue.

Placental cells may be obtained from a full-term or pre-term placenta. Placenta is preferably collected once it has been ex blooded. The placenta is preferably perfused for a period of time sufficient to remove residual cells (e.g., blood).

The term "perfuse" or "perfusion" used herein refers to the act of pouring or passaging a fluid over the placenta or in the later stages of the method over the cultured cells. The placental tissue may be from any mammal; for example, the placental tissue is human. A convenient source of placental tissue is from a post partum placenta (e.g., 1-6 hours), however, the source of placental tissue or cells or the method of isolation of placental tissue is not critical to the invention.

Placenta derived adherent cells may be obtained from both fetal (i.e., amnion, chorion, chorionic villi or inner parts of the placenta, see Example 1) and maternal (i.e., decidua basalis, and decidua parietalis) parts of the placenta. Tissue specimens are washed in a physiological buffer [e.g., phosphate-buffered saline (PBS) or Hank's buffer]. Single-cell suspensions are made by treating the tissue with a digestive enzyme (see below) or/and mincing and flushing the tissue parts through a nylon filter or by gentle pipetting (Falcon, Becton, Dickinson, San Jose, Calif.) with washing medium.

It will be appreciated that adherent cells may be derived from adipose tissue. Adipose tissue derived adherent cells may be isolated by a variety of methods known to those skilled in the art. For example, such methods are described in U.S. Pat. No. 6,153,432. The adipose tissue may be derived from omental/visceral, mammary, gonadal, or other adipose tissue sites. One source of adipose tissue is omental adipose. In humans, the adipose is typically isolated by liposuction.

Isolated adherent cells from placenta or adipose tissue may be derived by treating the tissue with a digestive enzyme such as collagenase, trypsin and/or dispase; and/or effective concentrations of hyaluronidase or DNAse; and ethylenediaminetetra-acetic acid (EDTA); at temperatures between 25-50° C., for periods of between 10 minutes to 3 hours. The cells may then be passed through a nylon or cheesecloth mesh filter of between 20 microns to 1 mm. Cells are centrifuged at speeds of between 100 to 3000×g for periods of between 1 minutes to 1 hour at temperatures of between 4-50° C. (see U.S. Pat. No. 7,078,230).

Cell retrieval from placenta or adipose tissue is preferably effected under aseptic conditions. Once isolated cells are obtained, they are allowed to adhere to an adherent material (e.g., configured as a surface) to thereby isolate adherent cells.

As used herein "an adherent material" refers to a synthetic, naturally occurring or a combination of same of a non-cytotoxic (i.e., biologically compatible) material having a chemical structure (e.g., charged surface exposed groups) which may retain the cells on a surface.

Examples of adherent materials which may be used in accordance with this aspect of the invention include, but are not limited to, a polyester, a polypropylene, a polyalkylene, a polyfluorochloroethylene, a polyvinyl chloride, a polystyrene, a polysulfone, a cellulose acetate, a glass fiber, a ceramic particle, a matrigel, an extra cellular matrix component (e.g., fibronectin, vitronectin, chondronectin, laminin), a collagen, a poly L lactic acid, a dextran and an inert metal fiber.

Further steps of purification or enrichment for stromal stem cells may be effected using methods which are well known in the art (such as by FACS using stromal stem cell marker expression, as further described herein below).

Non-limiting examples of base media useful in culturing according to the invention include Minimum Essential Medium Eagle, ADC-1, LPM (Bovine Serum Albumin-free), F10(HAM), F12 (HAM), DCCM1, DCCM2, RPMI 1640, BGJ Medium (with and without Fitton-Jackson Modification), Basal Medium Eagle (BME—with the addition of Earle's salt base), Dulbecco's Modified Eagle Medium (DMEM-without serum), Yamane, IMEM-20, Glasgow Modification Eagle Medium (GMEM), Leibovitz L-15 Medium, McCoy's 5A Medium, Medium M199 (M199E—with Earle's sale base), Medium M199 (M199H—with Hank's salt base), Minimum Essential Medium Eagle (MEM-E—with Earle's salt base), Minimum Essential Medium Eagle (MEM-H—with Hank's salt base) and Minimum Essential Medium Eagle (MEM-NAA with non essential amino acids), among numerous others, including medium 199, CMRL 1415, CMRL 1969, CMRL 1066, NCTC 135, MB 75261, MAB 8713, DM 145, Williams' G, Neuman & Tytell, Higuchi, MCDB 301, MCDB 202, MCDB 501, MCDB 401, MCDB 411, MDBC 153. A preferred medium for use in the invention is DMEM. These and other useful media are available from GIBCO, Grand Island, N.Y., USA and Biological Industries, Bet HaEmek, Israel, among others. A number of these media are summarized in Methods in Enzymology, Volume LVIII, "Cell Culture", pp. 62 72, edited by William B. Jakoby and Ira H. Pastan, published by Academic Press, Inc.

The medium may be supplemented such as with serum such as fetal serum of bovine or human or other species, and optionally or alternatively, growth factors, vitamins (e.g. ascorbic acid), cytokines, salts (e.g. B-glycerophosphate), steroids (e.g. dexamethasone) and hormones e.g., growth hormone, erythropoietin, thrombopoietin, interleukin 3, interleukin 6, interleukin 7, macrophage colony stimulating factor, c-kit ligand/stem cell factor, osteoprotegerin ligand, insulin, insulin like growth factors, epidermal growth factor, fibroblast growth factor, nerve growth factor, cilary neurotrophic factor, platelet derived growth factor, and bone morphogenetic protein at concentrations of between picogram/ml to milligram/ml levels.

It is further recognized that additional components may be added to the culture medium. Such components may be antibiotics, antimycotics, albumin, amino acids, and other components known to the art for the culture of cells. Additionally, components may be added to enhance the differentiation process when needed (see further below).

As mentioned, once adherent cells are at hand they may be passaged to two dimensional or three dimensional settings (see Examples 1 and 2 of the Examples section which follows). It will be appreciated though, that the cells may be transferred to a 3D-configured matrix immediately after isolation or alternatively, may be passaged to three dimensional settings following two dimensional (2D) conditions (as mentioned hereinabove).

It will be appreciated that during the 2D culturing conditions, the adherent cells may be continuously passaged. According to an embodiment of the present invention, the cells may be passaged for at least 4 passages, at least 5 passages, at least 6 passages, at least 7 passages or at least 8 passages. It will be appreciated that cells are typically passaged when the culture reaches about 70-90% confluence, typically after 3-7 days (e.g., 3-5 days, 1-3 doublings). Moreover, under the 2D culturing conditions, the cells may be grown in a culture medium devoid of antibiotic supplements from at least passage 2, at least passage 3, or at least passage 4.

Thus, the adherent material of this aspect of the invention is configured for 3D culturing thereby providing a growth matrix that substantially increases the available attachment surface for the adherence of the cells so as to mimic the infrastructure of the tissue (e.g., placenta).

For high scale production, culturing can be effected in a 3D bioreactor.

Examples of such bioreactors include, but are not limited to, a plug flow bioreactor, a continuous stirred tank bioreactor, a stationary-bed bioreactor (packed bed bioreactor) and a fluidized bed bioreactor.

As shown in Example 2 of the Examples section, the Celligen bioreactor is capable of 3D expansion of adherent cells under controlled conditions (e.g. pH, temperature and oxygen levels) and with constant cell growth medium perfusion. Furthermore, the cell cultures can be monitored for concentration levels of glucose, lactate, glutamine, glutamate and ammonium. The glucose consumption rate and the lactate formation rate of the adherent cells enable to measure cell growth rate and to determine the harvest time.

Other 3D bioreactors that can be used with the invention include, but are not limited to, a continuous stirred tank bioreactor, where a culture medium is continuously fed into the bioreactor and the used medium is continuously drawn out, to maintain a time-constant steady state within the bioreactor. The stirred tank bioreactor may be used with fluidized bed (suspended carriers) or a fibrous bed basket (which is available for example at New Brunswick Scientific Co., Edison, N.J.), a stationary-bed bioreactor, an air-lift bioreactor, where air is typically fed into the bottom of a central draught tube flowing up while forming bubbles, and disengaging exhaust gas at the top of the column, a bioreactor with Polyactive foams [as described in Wendt, D. et al., Biotechnol Bioeng 84:

205-214, (2003)], a porous scaffolds in a Radial-flow perfusion bioreactor [as described in Kitagawa et al., Biotechnology and Bioengineering 93(5): 947-954 (2006)], a radial flow bioreactor with scaffold or carriers, a hollow fiber bioreactor, and micro carriers. Other bioreactors which can be used in accordance with the invention are described in U.S. Pat. Nos. 6,277,151, 6,197,575, 6,139,578, 6,132,463, 5,902,741 and 5,629,186.

In an exemplary embodiment a total of $150\pm50\times10^6$ cells are seeded, $3$-$7\times10^6$ cell/gr carrier are seeded, or $0.06$-$0.13\times10^6$ cell/ml are seeded. According to an exemplary embodiment, cell seeding is effected at 1400-7000 cells/cm$^2$ FibraCel disks.

Cells can be harvested when at least about 10% of cells are proliferating while avoiding uncontrolled differentiation and senescence.

Culturing is effected for at least about 2 days, 3 days, 4 days, 5 days, 6 days, 7 days, 10 days, 14 days, 20 days, a month or even more. It will be appreciated that culturing in a bioreactor may prolong this period. Culturing of the adherent cells in the 3D culture can be effected under a continuous flow of a culture medium. Passaging may also be effected to increase cell number. It will be appreciated that culture medium may be changed in order to prolong and improve culturing conditions.

According to an embodiment of the present invention, the cell culturing is effected under perfusion of the culture medium. Typically, the perfusion rate is determined by the glucose concentration in the culture medium of the adherent cells. Thus, according to the present teachings, the culture medium may be changed when the glucose concentration is about 500 mg/L, about 550 mg/L; or about 600 mg/L.

Adherent cells of some embodiments of the present invention comprise at least about 10%, 28%, 30%, 50%, 80% or more proliferative cells (as can be assayed by FACS monitoring S and G2/M phases).

Adherent cells of some embodiments of the invention may comprise at least one "stromal stem cell phenotype".

As used herein "a stromal stem cell phenotype" refers to a structural or functional phenotype typical of a bone-marrow derived stromal (i.e., mesenchymal) stem cell.

As used herein the phrase "stem cell" refers to a cell which is not terminally differentiated.

Thus for example, the cells may have a spindle shape. Alternatively or additionally the cells may express a marker or a collection of markers (e.g. surface marker) typical to stromal stem cells. Examples of stromal stem cell surface markers (positive and negative) include but are not limited to CD105+, CD29+, CD44+, CD73+, CD90+, D7-fib+, CD3−, CD4−, CD34−, CD45−, CD80−, CD5−, CD20−, CD11B−, CD14−, CD19−, CD79−, HLA-DR−, CD31−, KDR−, and FMC7−. Other stromal stem cell markers include but are not limited to tyrosine hydroxylase, nestin and H-NF.

Adherent cells of placenta tissue generated according to the present teachings have a gene expression profile essentially as described in Example 3 of the Examples section which follows.

Examples of functional phenotypes typical of stromal stem cells include, but are not limited to, T cell suppression activity (they don't stimulate T cells and conversely suppress same) and hematopoietic stem cell support activity.

According to an exemplary embodiment, the adherent cells of the present invention are less committed to differentiation into osteogenic or adipogenic lineages as compared to adherent cells from the bone marrow grown and differentiated under the same conditions (see Examples 4-5 and Examples 6-7, respectively).

As is shown in Examples 3 of the Examples section which follows, the adherent cells of the present invention were found to suppress the immune reaction of human mononuclear cells in a mixed lymphocyte reaction (MLR) assay, thus exhibit biological activities which may be preferentially used in the clinic (e.g., T cell suppression activity, hematopoietic stem cell support activity).

According to one embodiment of the invention, the adherent cells of the invention are capable of suppressing immune reaction in a subject.

As used herein the phrase "suppressing immune reaction in a subject" refers to decreasing or inhibiting the immune reaction occurring in a subject in response to an antigen (e.g., a foreign cell or a portion thereof). The immune response which can be suppressed by the adherent cells include the humoral immune responses, and cellular immune responses, which involve specific recognition of pathogen antigens via antibodies and T-lymphocytes (proliferation of T cells), respectively.

The populations of cells generated according to the present teachings may be used for treating a condition which can benefit from cell or organ transplantation.

As used herein, the term "condition" refers to any pathology (disease, condition, syndrome or disorder) which may benefit from cell (e.g. stem cell) or organ transplantation. Examples include ischemic conditions, cardiovascular conditions, nervous system conditions, gastrointestinal tract conditions, orthopedic conditions, hematopoietic conditions, renal conditions and hepatic conditions, such as but are not limited to, peripheral arterial disease (PAD), such as limb ischemia and critical limb ischemia (CLI), lower extremity ischemia, ischemic vascular disease, ischemic heart disease, myocardial ischemia, acute myocardial infarction (MI), coronary artery disease (CAD), atherosclerotic cardiovascular disease, left main coronary artery disease, arterial occlusive disease, peripheral ischemia, peripheral vascular disease, arteriosclerosis, ischemic brain disease, stroke, cerebral ischemia, cerebro vascular disease, retinopathy, retinal repair, remodeling disorder, von Hippel-Lindau syndrome, hereditary hemorrhagic telengiectasiaischemic vascular disease, Buerger's disease, diabetes, vascular disease of the kidney, ischemic renal disease, liver disease, ischemic placenta, reproduction associated disorders, graft-versus-host disease (GVHD), solid organ transplant, hematopoietic stem cell transplantation (HSCT), metabolic disorders, inflammatory conditions of the gastrointestinal (GI) tract [e.g. inflammatory bowel disease (IBD)], ulcerative colitis, delayed wound-healing, delayed ulcer healing, cancer (e.g. breast cancer), pre-cancer, conditions characterized by connective tissue damage such as bone cancer, osteosarcoma, bone metastases, bone fracture, degenerative disc disease, osteogenesis imperfecta (OI), burn, burn wound, articular cartilage defect, wound healing, deep wound, delayed wound-healing, delayed ulcer healing, subchondral-bone cyst, osteoporosis, osteoarthritis (OA), degenerated bone, cartilage damage, articular cartilage defect, injured tendons (e.g. overstrain-induced injuries of tendons) and injured ligaments.

It will be appreciated that the adherent cells of the present invention are capable of inducing immunosuppression and/or tolerance in a subject. Thus, the adherent cells may be used to treat any condition in need of immunosuppression and/or tolerance. Such conditions included, but are not limited to, autoimmune diseases and inflammatory diseases (including acute and chronic inflammatory diseases) including, but are not limited to, cardiovascular diseases, rheumatoid diseases, glandular diseases, gastrointestinal diseases, cutaneous diseases, hepatic diseases, neurological diseases (e.g., neuropathic pain, peripheral nerve injury), muscular diseases, nephric diseases, support for renal transplantation, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J. Cardiol. 1999 Jun. 17; 83 (12A):75H), thrombocytopenic purpura (Moccia F. Ann Ital Med. Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt HO. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid, psoriasis and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med. Sci. 2000 April; 319 (4):234), myasthenia, Lambert-Eaton myasthenic syndrome (Takamori M. Am J Med. Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad. Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Furthermore, the adherent cells of the present invention may be used to treat diseases associated with transplantation of a graft including, but are not limited to, graft rejection, chronic graft rejection, subacute graft rejection, hyperacute graft rejection, acute graft rejection and graft versus host disease.

As used herein the term "treating" refers to inhibiting or arresting the development of a pathology and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology. The term "treating" may also refer to alleviating or diminishing a symptom associated with the pathology.

The subject treated by the adherent cells may be any subject (e.g., a mammal), such as a human subject or a domesticated animal including, but not limited to, horses (i.e. equine), cattle, goat, sheep, pig, dog, cat, camel, alpaca, llama and yak who is diagnosed with or suffers from the pathology and can benefit from stromal stem cell transplantation.

Methods of deriving lineage specific cells from the adherent cells (e.g. stromal stem cells) of the invention are well known in the art. See for example, U.S. Pat. Nos. 5,486,359, 5,942,225, 5,736,396, 5,908,784 and 5,902,741.

The adherent cells may be naïve or may be genetically modified such as to derive a lineage of interest (see U.S. Pat. Appl. No. 20030219423).

The cells may be of autologous or non-autologous source. A non-autologous source may be allogeneic or xenogeneic. Cells may be used as fresh or frozen (e.g., cryo-preserved) preparations.

Depending on the medical condition, the subject may be administered with additional chemical drugs (e.g., immunomodulatory, chemotherapy etc.) or cells.

Even though the cells are characterized by immuno-suppressive activity, they may still provoke host or donor-derived undesirable immune response. Approaches have been developed to reduce the likelihood of rejection of non-autologous cells or GvHD. These include either suppressing the recipient immune system or encapsulating the non-autologous cells in immunoisolating, semipermeable membranes before transplantation.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu M Z, et al., Cell encapsulation with alginate and alpha-phenoxycinnamylidene-acetylated poly(allylamine). Biotechnol Bioeng. 2000, 70: 479-83, Chang T M and Prakash S. Procedures for microencapsulation of enzymes, cells and genetically engineered microorganisms. Mol. Biotechnol. 2001, 17: 249-60, and Lu M Z, et al., A novel cell encapsulation method using photosensitive poly(allylamine alpha-cyanocinnamylidene-acetate). J. Microencapsul. 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 μm. Such microcapsules can be further encapsulated with additional 2-5 μm ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Technol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 μm (Canaple L. et al., Improving cell encapsulation through size control. J Biomater Sci Polym Ed. 2002; 13:783-96). Moreover, nanoporous biocapsules with well-controlled pore size as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE), etanercept, TNFalpha blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

Furthermore, it will be appreciated that the cells can be administered either per se or, preferably as a part of a pharmaceutical composition that further comprises a pharmaceutically acceptable carrier.

As used herein a "pharmaceutical composition" refers to a preparation of the adherent cells of the invention (i.e., adherent cells), with other chemical components such as pharmaceutically suitable carriers and excipients. The purpose of a pharmaceutical composition is to facilitate administration of the cells to a subject.

Hereinafter, the term "pharmaceutically acceptable carrier" refers to a carrier or a diluent that does not cause significant irritation to a subject and does not abrogate the biological activity and properties of the administered compound. Examples, without limitations, of carriers are propylene glycol, saline, emulsions and mixtures of organic solvents with water.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Pharmaceutical compositions for use in accordance with the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, physiological salt buffer, or freezing medium containing cryopreservents.

Determination of a therapeutically effective amount is well within the capability of those skilled in the art, especially in light of the detailed disclosure provided herein.

Toxicity and therapeutic efficacy of the active ingredients described herein can be determined by standard pharmaceutical procedures in vitro, in cell cultures or experimental animals.

Depending on the severity and responsiveness of the condition to be treated, dosing can be of a single or a plurality of administrations. However, the amount of a composition to be administered will, of course, be dependent on the subject being treated, the severity of the affliction, the manner of administration, the judgment of the prescribing physician, etc.

Compositions including the preparation of the invention formulated in a compatible pharmaceutical carrier may also be prepared, placed in an appropriate container, and labeled for treatment of an indicated condition.

Compositions of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

It is expected that during the life of a patent maturing from this application many relevant three dimensional cultures will be developed and the scope of the term three dimensional cultures is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Production of Placenta Derived Adherent Cells by the Methods of WO/2007/108003

Adherent cells were produced as was previously described (see WO/2007/108003) in a bioreactor system containing 3D carriers to produce adherent cells (designated herein as PLX).

Materials and Experimental Procedures

Placenta derived adherent cells—Inner parts of a full-term delivery placenta (Bnei Zion medical center, Haifa, Israel) were cut under aseptic conditions, washed 3 times with Hank's Buffer and incubated for 3 hours at 37° C. with 0.1% Collagenase (1 mg/ml tissue; Sigma-Aldrich, St. Lewis, Mo.). Using gentle pipetting, suspended cells were then washed with DMEM supplemented with 10% FCS, Pen-Strep-Nystatin mixture (100 U/ml:100 μg/ml:1.25 un/ml) and 2 mM L-glutamine, seeded in 75 cm² flasks and incubated at 37° C. in a tissue culture incubator under humidified condition with 5% $CO_2$.

Two Dimensional (2D) Cell Growth

Cells were allowed to adhere to a plastic surface for 48-72 hours after which the media was changed every 3-4 days. After 2-3 passages, the cells were cryopreserved, thawed and seeded for a secondary growth in flasks. When reaching 60-80% confluence cells were detached from the growth flask using 0.25% trypsin-EDTA and seeded into new flasks (usually every 3-5 days), for another 2-5 passages. Cultured cells were thereafter collected for analysis or for culturing in bioreactors.

PluriX™ Plug Flow bioreactor—The PluriX™ Plug Flow bioreactor (Pluristem, Haifa, Israel; as was previously described in U.S. Pat. No. 6,911,201 and WO/2007/108003), was loaded with 1-100 ml packed 3D porrosive carriers (4 mm in diameter) made of a non woven fabric matrix of polyester. These carriers enable the propagation of large cell numbers in a relatively small volume. Glassware was designed and manufactured by Pluristem (Pluristem, Haifa, Israel). The bioreactor was maintained in an incubator of 37° C., with flow rate regulated and monitored by a valve and peristaltic pump. The bioreactor contains a sampling and injection point, allowing the sequential seeding of cells. Culture medium was supplied at pH 6.7-7.4 from a reservoir. The reservoir was supplied by a filtered gas mixture containing air/$CO_2$/$O_2$ at differing proportions, depending on cell density in the bioreactor. The $O_2$ proportion was suited to the level of dissolved $O_2$ at the bioreactor exit, determined by a monitor. The gas mixture was supplied to the reservoir via silicone tubes or diffuser (Degania Bet, Emek Hayarden, Israel). The culture medium was passed through a separating container which enables collection of circulating, non-adherent cells. Circulation of the medium was obtained by a peristaltic pump. The bioreactor was further equipped with an additional sampling point and containers for continuous medium exchange.

Production of PLX adherent cells—Non-confluent primary human adherent 2D cell cultures, grown as described above, were trypsinized, washed, resuspended in DMEM supplemented with 10% FBS, Pen-Strep-Nystatin mixture (100 U/ml:100 ug/ml:1.25 un/ml) and 2 mM L-glutamine, and seeded ($10^3$-$10^5$ cells/ml) via an injection point onto the 3D carriers in a sterile Plug Flow bioreactor. Prior to inoculation, bioreactor was filled with PBS-Ca—Mg (Biological Industries, Beit Ha'emek, Israel), autoclaved (120° C., 30 min) and washed with Dulbecco's growth medium containing 10% heat-inactivated fetal calf serum and a Pen-Strep-Nystatin mixture (100 U/ml:100 ug/ml:1.25 un/ml). Flow was kept at a rate of 0.1-5 ml/min. Seeding process involved cease of circulation for 2-48 hrs, thereby allowing the cells to settle on the carriers. Bioreactor was kept under controlled temperature (37° C.) and pH conditions (pH=6.7-7.4); using an incubator supplied with sterile air and $CO_2$ as needed. Growth medium was replaced 2-3 times a week. Circulation medium was replaced with fresh DMEM media, every 4 hr to 7 days. At a density of $1\times10^{-6}$-$1\times10^7$ cells/ml (following 12-40 days of growth), total medium volume was removed from the bioreactor and bioreactor and carriers were washed 3-5 times with PBS. PLX adherent cells were then detached from the carriers with Trypsin-EDTA; (Biological Industries, Beit Ha'emek, Israel; 3-15 minutes with gentle agitation, 1-5 times), and were thereafter resuspended in DMEM and cryopreserved.

Example 2

Production of the Placenta Derived Adherent Cells of the Present Invention

PLX-C adherent cells were produced by the present invention which exhibit different characteristics then the above described PLX adherent cells.

Materials and Experimental Methods

Celligen™ Plug Flow bioreactor—The production of adherent cells of the present invention by Celligen™ (PLX-C cells) is composed of several major steps as illustrated in FIG. 1. The process starts by collection of a placenta from a planned caesarean section at term.

Adherent cells are then isolated from whole placentas, grown in tissue culture flasks (2D cultures), harvested and stored in liquid nitrogen as 2D-Cell Stock (2DCS), the appropriate amount of 2DCS are thawed, washed and seeded onto carriers in bioreactors for further expansion as 3D-culture. After 4-12 days of growth in the bioreactors, cells are harvested and cryopreserved in gas phase of liquid nitrogen as PLX-C.

Receipt of Human Tissue

All placentas obtained were received from the maternity ward under approval of the Helsinki Committee of the medical facility. Accordingly, all placenta donors signed an informed consent and Donor Screening and Donor Testing was performed. Immediately after taking the placenta from the donor (during the caesarean procedure), it was placed in a sterile plastic bag and then in a temperature-preserving box with ice packs.

Recovery and Processing of Adherent Cells

To initiate the process, the placenta tissue was cut into pieces under aseptic conditions under laminar flow hood, washed with Hank's buffer solution and incubated for 2-5 hours at 37° C. with 0.1% Collagenase (1 mg Collagenase/ml tissue). 2D cell medium (2D-Medium comprising DMEM supplemented with 10% FBS, fungizone 0.25 μg/ml and Gentamycin 50 μg/ml) was added and the digested tissue was roughly filtered through a sterile metal strainer, collected in a sterile beaker and centrifuged (10 minutes, 1200 RPM, 4° C.). Using gentle pippeting, suspended cells were then diluted with 2D-Medium supplemented with antibiotics, seeded in 175 cm² flasks and incubated at 37° C. in a tissue culture incubator under humidified condition supplemented with 5% $CO_2$. Following 2-3 days, in which the cells were allowed to adhere to the flask surface, they were washed with PBS and 2D-Medium was added.

Two Dimensional (2D) Cell Growth

Prior to the first passage, growth medium samples of 10% of the total flask number in quarantine was pooled and taken for mycoplasma testing (IPC2). If cells were found to be negative for Mycoplasma (EZ-PCR Mycoplasma kit, Biological Industries, Israel), cells were released from quarantine. After 1-2 additional passages using 2D-Medium supplemented with antibiotics, cells were transferred to the 2D production clean room (2DP). Once in Room 2DP, culture was continued for another 3-6 passages using 2D-Medium without antibiotics. Throughout the process, cultures were grown in a tissue culture incubator under humidified conditions with 5% $CO^2$ at 37° C. After a total of 6-9 passages (9-17 cell doublings), cells were collected and cryopreserved as the 2D-Cell Stock (2DCS).

The first passage was usually carried out after 7-15 days. Beginning at passage 2 and continuing until passage 6-9, cells were passaged when the culture reached 70-90% confluence, usually after 4-5 days (1.5-2 doublings). The cells were detached from the flasks using 0.25% trypsin-EDTA (4 minutes at 37° C.) and seeded in a culture density of $4\pm0.5\times10^3$ cells/cm². The size of the tissue culture flasks raised as the passages proceed. The culturing process started in 175 cm² tissue culture flask, continued in 500 cm² (Triple flask) and finally the cells were seeded into Cell Factory 10 tray (6320 cm²).

Prior to cryopreservation, at the end of 2DCS growth period, the growth medium was collected and the sample was prepared to be sent to an approved GLP laboratory for Mycoplasma test (IPC 4).

Cryopreservation Procedure for 2D-Cell-Stock Product

For 2DCS cryopreservation, 2D-cultured cells were collected under aseptic conditions using 0.25% trypsin-EDTA. The cells were centrifuged (1200 RPM, 10', 4° C.), counted and re-suspended in 2D-Medium.

For freezing, cell suspensions were diluted 1:1 with 2D-Freezing Mixture (final concentrations was 10% DMSO, 40% FBS and 50% 2D-Medium). Approximately $1.5-2.5\times10^9$ cells were manufactured from one placenta. 4 ml of the cells were stored at a final concentration of $10\times10^6$/ml in 5 ml cryopreservation polypropylene vials. The vials were labeled and transferred to a controlled rate freezer for a graduated temperature reducing process (1° C./min), after which they were transferred to storage in gas-phase of a liquid nitrogen freezer. This material was referred to as the 2D-Cell Stock (2DCS) batch.

Initiation of the Three Dimensional (3D) Culture Procedures

To begin 3D culture, an appropriate amount ($150\pm50\times10^6$) of cells from 2DCS were thawed in the 2DP room and washed with 3D-Medium (DMEM with 10% FBS and 20 Mm Hepes) to remove DMSO prior to seeding in the prepared-in-advanced bioreactor systems. The content of each 2DCS vial was pipetted and diluted 1:9 with pre-warmed (37° C.) 3D-Medium. The cells were centrifuged (1200 RPM, 10', 4° C.) and re-suspended again in 50-100 ml pre-warmed (37° C.) 3D-Medium in a 250 ml sterile bottle. A sample was taken and cells were counted using a Trypan Blue stain in order to determine cell number and viability. The cell suspension was transferred under a laminar flow hood into a 0.5 L seeding bottle. From the seeding bottle the cell suspension was transferred via sterile tubing to the bioreactor by gravitation.

Production of Adherent Cells in the Celligen Bioreactor (PLX-C)

Figure 2:
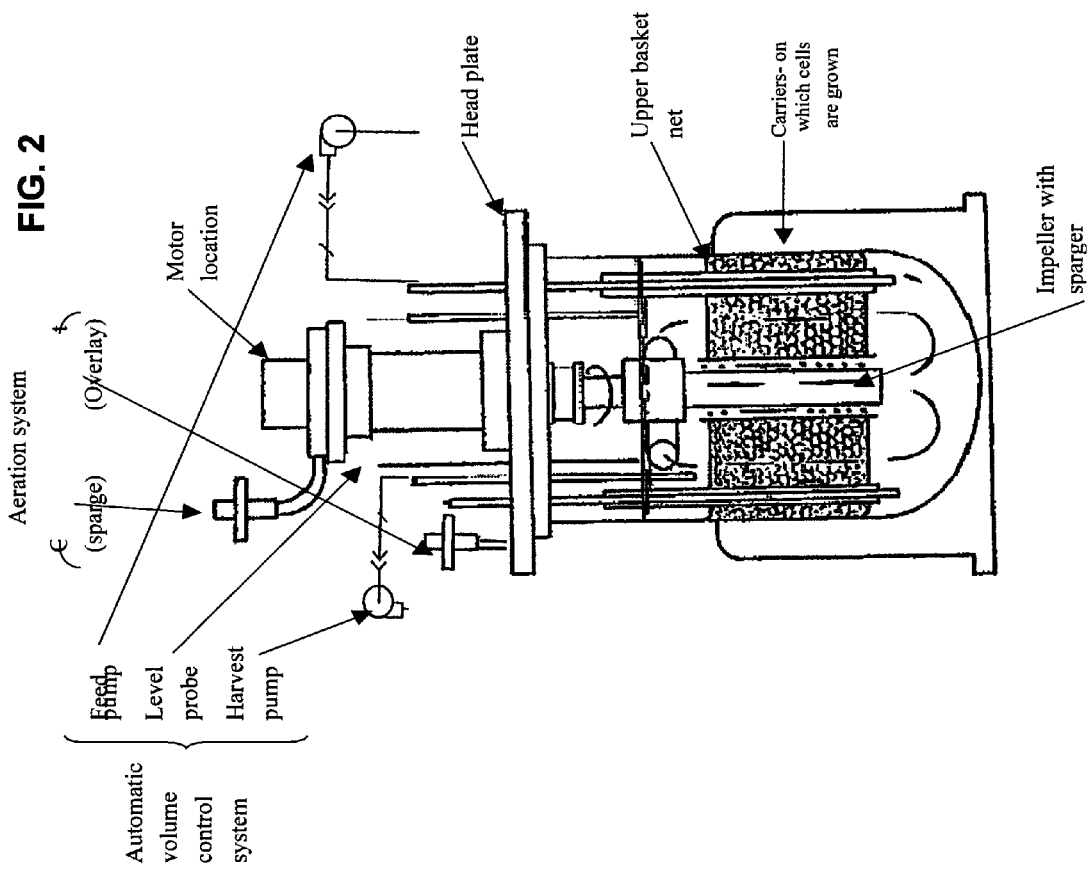
FIG. 2 is a diagram of an exemplary bioreactor vessel and ports adapted from The New Brunswick Scientific web site.

Bioreactor Description 3D growth phase was performed using an automatic CelliGen Plus® or BIOFLO 310 bioreactor system [(New Brunswick Scientific (NBS)] depicted in FIG. 2. The bioreactor system was used for cultivation of cell culture, in which conditions were suitable for high cell concentrations. The cultivation process was carried out using a bioreactor in a perfusion mode. The lab scale bioreactor was constructed of two main systems—the control system and the bioreactor itself (vessel and accessories). The parameters of the process were monitored and controlled by a control console which included connectors for probes, motor and pumps, control loops for Dissolved Oxygen (DO), pH, perfusion and agitation (with a motor), a gases control system, water circulation and heating system for temperature control and an operator interface. The controlled process parameters (such as temperature, pH, DO etc.) could be displayed on the operator interface and monitored by a designated controller.

Cell Culture Growth Procedure in the Bioreactors

As noted in the section hereinabove, $150\pm50\times10^6$ cells from the cryopreserved 2DCS were thawed, washed and seeded in a sterile bioreactor. The bioreactor contained 30-50 gr carriers (FibraCel® disks, NBS), made of Polyester and Polypropylene and $1.5\pm0.1$ L 3D-Medium. The growth medium in the bioreactor was kept at the following conditions: 37° C., 70% Dissolved Oxygen (DO) and pH 7.3. Filtered gases (Air, $CO_2$, $N_2$ and $O_2$) were supplied as determined by the control system in order to keep the DO value at 70% and the pH value at 7.3. For the first 24 hours, the medium was agitated at 50 Rounds Per Minutes (RPM) and increased up to 200 RPM by day 2. For the first 2-3 days, the cells were grown in a batch mode. Perfusion was initiated when the medium glucose concentration decreased below 550 mg/liter. The medium was pumped from the feeding container to the bioreactor using sterile silicone tubing. All tubing connections were performed under laminar flow using sterile connectors. The perfusion was adjusted on a daily basis in order to keep the glucose concentration constant at approximately $550\pm50$ mg\liter. A sample of the growth medium was taken every 1-2 days for glucose, lactate, glutamine, glutamate and ammonium concentration determination (BioProfile 400 analyzer, Nova Biomedical). The glucose consumption rate and the lactate formation rate of the cell culture enabled to measure cell growth rate. These parameters were used to determine the harvest time based on accumulated experimental data.

Harvest of the 3D Grown PLX-C Cells from the Bioreactor

The cell harvest process started at the end of the growth phase (4-12 days). Two samples of the growth medium were collected. One sample was prepared to be sent to an approved GLP laboratory for Mycoplasma testing according to USP and Eu standards. This medium sample was considered as part of the Mycoplasma testing of the final product and the results were considered as part of the criteria for product release.

The 3D-grown culture was harvested in the Class-100 laminar area in room 3DP as follows:

The bioreactor vessel was emptied using gravitation via tubing to a waste container. The bioreactor vessel was then refilled with 1.5 L pre-warmed PBS (37° C.). The agitation speed was increased to 150 RPM for 2 minutes. The PBS was drained via tubing by pressure or gravity to the waste bottle. The washing procedure was repeated twice.

In order to release the cells from the carriers, 1.5 L pre-warmed to 37° C. Trypsin-EDTA (Trypsin 0.25%, EDTA 1 mM) was added to the bioreactor vessel and carriers were agitated for 1-4 minutes in 150 RPM, 37° C. 250 ml FBS was added to the bioreactor vessel and the cell suspension was collected to a 5 L sterile container. Cell suspension was divided to 500 ml sterile centrifuge tubes which were centrifuged (1200 RPM, 10', 4° C.) and re-suspended in cryopreservation solution at a concentration of $5\text{-}30 \times 10^6$ cells/ml. Cells were aseptically filled and cryopreserved as PLX-C.

Example 3

Comparison of the Adherent Cells of WO/20071108003 (PLX) to the Adherent Cells of the Present Invention Adherent cells produced by WO/2007/108003 (designated herein as PLX), as described in Example 1 hereinabove, were compared to the new adherent cells of the present invention (designated herein as PLX-C).

Materials and Experimental Methods

Cell Cycle analysis—PLX-C cells obtained by Celligen and PLX cells obtained by Plurix were fixed with 70% EtOH O.N, centrifuged and re-suspended in a Propidium Iodide (PI) solution containing 2 µg/ml PI (Sigma), 0.2 mg/ml Rnase A (Sigma) and 0.1% (v/v) Triton (Sigma) for 30 minutes. Cell cycle was analyzed by FACS.

Gene expression array (Microarray)—Adherent cells were obtained from human full term placentas and were expanded Plurix or by Celligen. Three different batches of cells were obtained from each of the expansion methods for further examination.

RNA was extracted from the cells (Qiagen-Rneasy micro kit) and applied to an Affymetrix whole genome expression array. The chip used GeneChip® Human Exon 1.0 ST Array (Affymetrix, Santa Clara, Calif., USA).

FACS analysis of membrane markers—cells were stained with monoclonal antibodies as previously described. In short, 400,000-600,000 cells were suspended in 0.1 ml flow cytometer buffer in a 5 ml test tube and incubated for 15 minutes at room temperature (RT), in the dark, with each of the following monoclonal antibodies (MAbs): FITC-conjugated anti-human CD29 MAb (eBioscience), PE conjugated anti human CD73 MAb (Becton Dickinson), PE conjugated anti human CD105 MAb (eBioscience), PE conjugated anti human CD90 MAb (Becton Dickinson), FITC-conjugated anti-human CD45 MAb (IQProducts), PE-conjugated anti-human CD19 MAb (IQProducts), PE conjugated anti human CD14 MAb (IQProducts), FITC conjugated anti human HLA-DR MAb (IQProduct), PE conjugated anti human CD34 MAb (IQProducts), FITC conjugated anti human CD31 MAb (eBioscience), FITC conjugated anti human KDR MAb (R&D systems), anti human fibroblasts marker (D7-FIB) MAb (ACRIS), FITC-conjugated anti-human CD80 MAb (BD), FITC-conjugated anti-human CD86 MAb (BD), PE conjugated anti-human CD200 MAb (BD), FITC-conjugated anti-human CD40 MAb (BD), FITC-conjugated anti-human HLA-ABC MAb (BD), Isotype IgG1 FITC conjugated (IQ Products), Isotype IgG1 PE conjugated (IQ Products).

Cells were washed twice with flow cytometer buffer, resuspended in 500 µl flow cytometer buffer and analyzed by flow cytometry using FC-500 Flow Cytometer (Beckman Coulter). Negative controls were prepared with relevant isotype fluorescence molecules.

Mixed Lymphocyte Reaction (MLR)

$2 \times 10^5$ peripheral blood (PB) derived MNC (from donor A) were stimulated with equal amount of irradiated (3000 Rad) PB derived MNCs (from donor B). Increasing amounts of PLX-Cs were added to the cultures. Three replicates of each group were seeded in 96-well plates. Cells were cultured in RPMI 1640 medium containing 20% FBS. Plates were pulsed with 1 µC $^3$H-thymidine during the last 18 hrs of the 5-day culturing. Cells were harvested over a fiberglass filter and thymidine uptake was quantified with scintillation counter.

For CFSE staining, PB-MNC cells were stained for CFSE (Molecular Probes) for proliferation measurement before culturing. Cells were collected after 5 days and the intensity of CFSE staining was detected by Flow Cytometry.

ELISA

ELISA was carried out as was previously described. In short, MNCs (isolated from peripheral blood) were stimulated with 5 µg/ml ConA (Sigma), 0.5 µg/ml LPS (SIGMA), or 10 µg/ml PHA (SIGMA) in the presence of PLX-C under humidified 5% CO2 atmosphere at 37° C. Supernatants were collected and subjected to cytokine analysis using ELISA kits for IFNγ (DIACLONE), TNFα (DIACLONE) and IL-10 (DIACLONE).

Experimental Results

The changes in manufacturing with Celligen as compared to Plurix resulted in several major differences (summarized in Table 1, below).

TABLE 1

Comparison between Plurix system (WO/2007/108003) and Celligen system (teachings of the present invention)

| Parameter | WO/2007/108003 | Teachings of the present invention | Improvement |
|---|---|---|---|
| Working volume (ml) | 280 | 1500 | Scale up of the process. Higher production level in the present teachings (2-8 |

TABLE 1-continued

Comparison between Plurix system (WO/2007/108003) and Celligen system (teachings of the present invention)

| Parameter | WO/2007/108003 | Teachings of the present invention | Improvement |
|---|---|---|---|
| Weight of carrier (gr) | 1.4 | 30 | population doubling) Scale up of the process in the present teachings. |
| Bed configuration | Conic, 50 ml column | Cylinder Packed bed | The present teachings - Better flow of medium and nutrients. WO/2007/108003 - Inefficient flow due to narrow outlet form the conic structure Better homogeneity of medium flow. Channeling in the plurix |
| Cell concentration at seeding (cell/gr carrier) | $3 \times 10^6$ cell/gr carrier | $5 \times 10^6$ cell/gr carrier | Better cell to cell interaction in the present teachings |
| Cell concentration at seeding (cell/ml) | $0.015 \times 10^6$ cell/ml | $0.1 \times 10^6$ cell/ml | Better cell to cell interaction in the present teachings |
| Seeding procedure | Seeding at low medium volume for 24 h followed by addition of medium to final working volume | Seeding at the final working volume while agitating | WO/2007/108003 - Heterogenic distribution of the cell culture inside the carrier bed Insufficient medium volume in the first 24 h of the run. Leading to unsuitable working conditions (acidic environment) |
| Production phase duration | 14-21 days | 4-12 days | Better product quality. Efficient harvest process. Better yield. Lower cost process in the present teachings |
| Mode of operation | Repeated batch - medium change twice a week | Perfusion mode - rate was adjusted according to the glucose concentration (the medium was changed at glucose concentration of $550 \pm 50$ mg/L) | Present teachings - Moderate changes of the conditions regarding medium composition throughout the run Continuous removal of toxic agents produced by the cells. In batch mode - lower concentration of essential nutrients (limiting factors) Less cell debris |

TABLE 1-continued

Comparison between Plurix system (WO/2007/108003) and Celligen system (teachings of the present invention)

| Parameter | WO/2007/108003 | Teachings of the present invention | Improvement |
|---|---|---|---|
| Harvest procedure | Harvesting in 50 ml tubes Trypsinization 3 cycles | Harvesting inside the bioreactor Trypsinization 1 cycle | Present teachings - More efficient process Harvest is carried out in a close system. 1 trypsinization cycle - better quality of the cells. |
| Agitation | medium Circulation between reservoir container to the column using peristaltic pump | Cell lift impeller | Present teachings - Medium is flowing through the packed bed - Better supply of nutrients and oxygen to the culture. Homogeneity of the medium Improves other control loops (temp., DO, pH) |
| Temperature control | The production was carried out inside an incubator. Indirect temperature control (of the incubator chamber). Heat transfer via air interface | On-line direct control. Heat transfer via water jacket. | Present teachings - more accurate measurement of the culture temperature. Quick response. Short time to reach set point. |
| Temperature monitoring | Manually. Indirect water temperature monitoring. | On-line direct monitoring. | Present teachings - Better monitoring and control of the process. Quick response to malfunctions. |
| DO monitoring | None | On-line monitoring | Present teachings - Better monitoring and control of the process. Quick response to malfunctions |
| DO control | None. Introduction of air only | On-line direct control of a specific set point using Air, $O_2$ and $N_2$. | Present teachings - Better control of DO level. Better maintenance of a specified working conditions |
| pH monitoring and control | Only visual monitoring (Phenol red as part of the medium) | On-line Control and monitoring | Present teachings - Better control of pH level. Better maintenance of a specified working conditions |
| Aeration | Sparge only | Overlay (sparge as an option) | WO/2007/108003 - Aeration by sparge creates foam that might damage the cells. |

The changes in the manufacturing process resulted in changes in characteristics of the obtained adherent cells. These differences are summarized below.

Figure 3A:
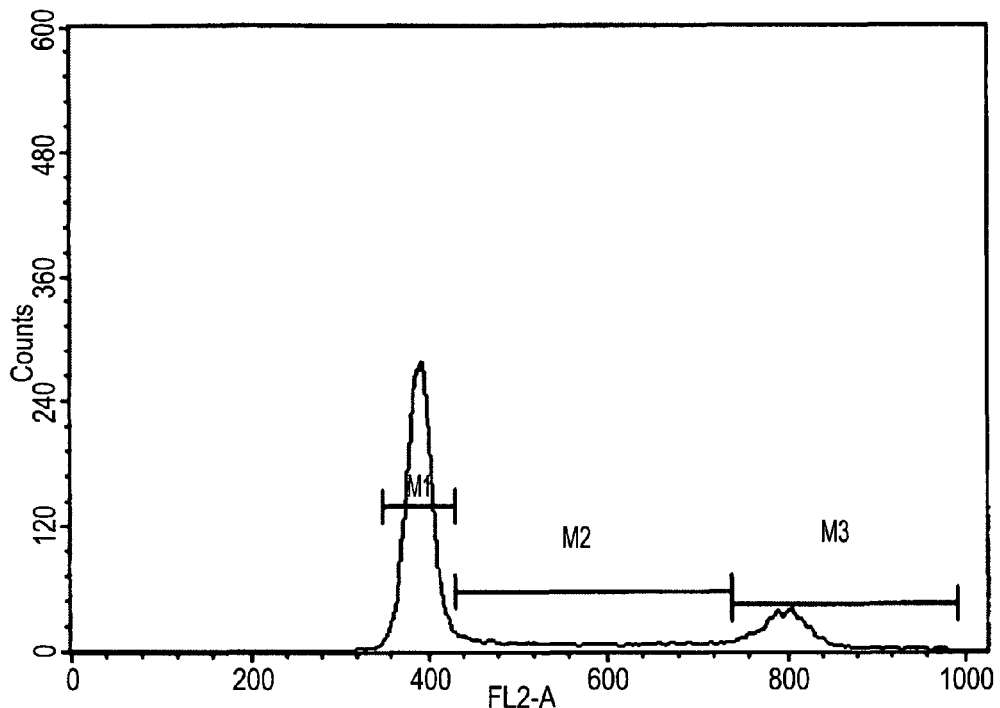
FIGS. 3A-B depict cell cycle analysis of 3D adherent cells manufacture by Plurix (designated PLX, FIG. 3B) and by the present teachings (PLX-C, FIG. 3A). Cells were fixed in 70% EtOH O.N, centrifuged and re-suspended in a Propidium Iodide (PI) solution and then analyzed by FACS.
Figure 3B:
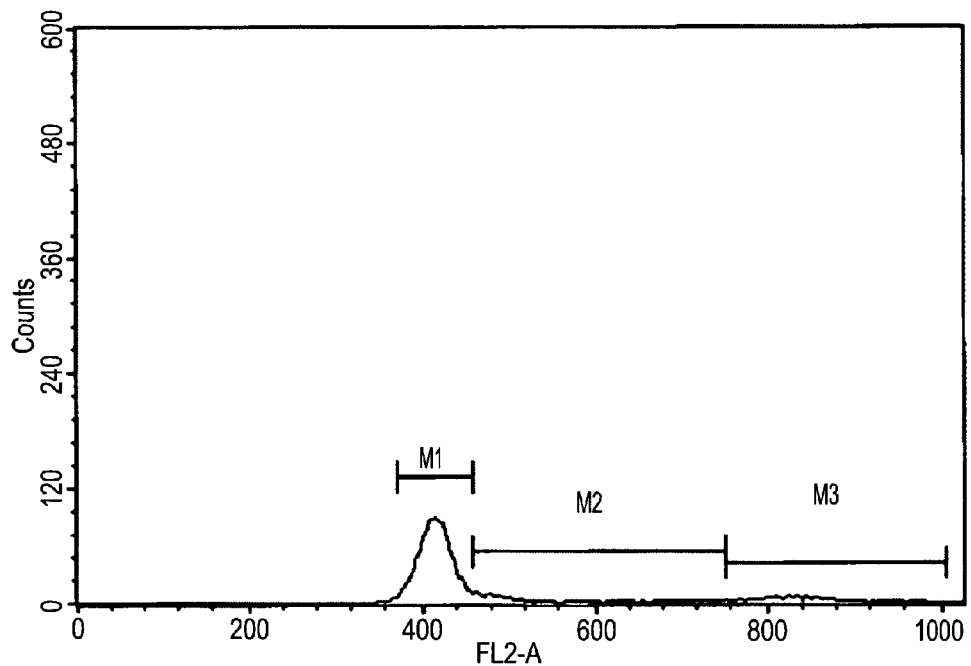

Cell cycle analysis of PLX manufactured by Plurix compared to PLX-C manufactured by Celligen—PLX-C cells obtained by Celligen were compared to PLX cells obtained by Plurix in order to examine the distribution of the cells between the different phases of the cell cycle. As is clear from FIGS. 3A-B, PLX-C cells expanded by Celligen exhibited typical proliferating profile (distribution of cells between the different phases of cell cycle). Specifically, 28% of cells were in S and G2/M phases (FIG. 3A). These results indicated that cells were harvested during proliferation and that the Celligen bioreactor conditions supported cell growth.

Microarray comparison between Plurix and Celligen obtained cells—gene expression arrays enabled to simultaneously monitor genome-wide expression profiles of adherent cells derived from human full term placentas expanded by Plurix (PLX) or by Celligen (PLX-C). These results enabled to assess the molecular mechanism underlying phenotypic variation between cells obtained by these different growth methods (see Table 2, below).

TABLE 2

Gene expression in Plurix cells (WO/2007/108003) compared to Celligen cells (teachings of the present invention)

| Gene | Celligen vs Plurix (fold change) | p-value (treat) |
|---|---|---|
| interferon-induced protein with tetratricopeptide repeats | 17.52 | 0.0401812 |
| aldehyde dehydrogenase 1 family, member A1 | 16.76 | 0.00145807 |
| leukocyte-derived arginine aminopeptidase | 13.99 | 3.88E−06 |
| keratin 27 pseudogene 27 | 12.25 | 0.000224998 |
| similar to Keratin, type I cytoskeletal 18 (Cytokerati | 11.83 | 0.000304949 |
| G protein-coupled receptor, family C, group 5, member A | 10.35 | 3.39E−05 |
| integrin, alpha 6 | 9.84 | 0.0411667 |
| G protein-coupled receptor 126 | 8.73 | 0.00197635 |
| coagulation factor III (thromboplastin, tissue factor) | 7.36 | 0.012192 |
| Rho GDP dissociation inhibitor (GDI) beta | 7.36 | 0.00200066 |
| signal peptide, CUB domain, EGF-like 3 | 7.20 | 0.0255115 |
| interferon-induced protein with tetratricopeptide repeats | 7.09 | 0.0139777 |
| dickkopf homolog 1 (*Xenopus laevis*) | 7.06 | 3.06E−07 |
| NAD(P)H dehydrogenase, quinone 1 | 6.63 | 0.000282423 |
| keratin 18 | 6.46 | 0.000514523 |
| opioid growth factor receptor-like 1 | 5.96 | 0.00114551 |
| mal, T-cell differentiation protein-like | 5.95 | 0.00664216 |
| neurofilament, medium polypeptide 150 kDa | 5.86 | 0.0190611 |
| DEP domain containing 1 | 5.82 | 0.000370513 |
| cathepsin C | 5.72 | 0.00532262 |
| WAS | 5.47 | 0.00178153 |
| serpin peptidase inhibitor, clade B (ovalbumin), member | 5.44 | 0.0190218 |
| solute carrier family 7, (cationic amino acid transporte | 5.33 | 0.00688017 |
| interferon-induced protein with tetratricopeptide repea | 5.18 | 0.00357376 |
| NUF2, NDC80 kinetochore complex component, homolog (S. cere | 5.05 | 0.00276524 |
| SHC SH2-domain binding protein 1 | 4.95 | 0.00430878 |
| thioredoxin reductase 1 | 4.86 | 0.000197486 |
| lung cancer metastasis-associated protein | 4.85 | 0.00148024 |
| Rho GTPase activating protein 29 | 4.85 | 0.0466211 |
| cell division cycle 20 homolog (*S. cerevisiae*) | 4.80 | 0.00514206 |
| family with sequence similarity 111, member B | 4.63 | 0.000125819 |
| PDZ binding kinase | 4.54 | 0.00784983 |
| establishment of cohesion 1 homolog 2 (*S. cerevisiae*) | 4.53 | 0.000773033 |
| guanylate binding protein 4 | 4.47 | 0.000215944 |
| lipase A, lysosomal acid, cholesterol esterase (Wolman dise | 4.42 | 0.0167385 |
| kinesin family member 20A | 4.39 | 0.00582352 |
| KIAA0101 | 4.28 | 0.0105909 |
| cyclin-dependent kinase inhibitor 3 (CDK2-associated dual | 4.25 | 0.000732492 |
| thymidylate synthetase | 4.23 | 0.00685584 |
| chromosome 13 open reading frame 3 | 4.18 | 0.000548296 |
| aurora kinase A | 4.16 | 0.00632571 |
| nei endonuclease VIII-like 3 (*E. coli*) | 4.14 | 0.00115606 |
| centrosomal protein 55 kDa | 4.13 | 0.0021952 |
| oxidized low density lipoprotein (lectin-like) receptor 1 | 4.11 | 0.0205198 |
| denticleless homolog (*Drosophila*) | 4.05 | 0.00141153 |
| anillin, actin binding protein | 4.01 | 0.010923 |
| ribonucleotide reductase M2 polypeptide | 3.98 | 0.00834059 |
| ankyrin repeat domain 1 (cardiac muscle) | 3.93 | 0.00911953 |
| transcription factor 19 (SC1) | 3.89 | 0.00109627 |
| keratin 18 | 3.89 | 0.000112551 |
| non-SMC condensin I complex, subunit G | 3.88 | 0.00537097 |
| cyclin E2 | 3.87 | 0.000203389 |

TABLE 2-continued

Gene expression in Plurix cells (WO/2007/108003) compared to Celligen cells (teachings of the present invention)

| Gene | Celligen vs Plurix (fold change) | p-value (treat) |
|---|---|---|
| trypsinogen C | 3.86 | 0.00416276 |
| small nucleolar RNA, C | 3.81 | 0.0334484 |
| tight junction protein 2 (zona occludens 2) | 3.81 | 0.00012562 |
| kinesin family member 18A | 3.78 | 0.00134108 |
| kinesin family member 2C | 3.77 | 0.0059888 |
| shugoshin-like 1 (S. pombe) | 3.76 | 0.00101318 |
| polo-like kinase 1 (Drosophila) | 3.75 | 0.0140309 |
| thymidine kinase 1, soluble | 3.73 | 0.00124134 |
| transcription factor 19 (SC1) | 3.73 | 0.00124327 |
| transcription factor 19 (SC1) | 3.73 | 0.00124327 |
| claspin homolog (Xenopus laevis) | 3.71 | 0.00683624 |
| GINS complex subunit 1 (Psf1 homolog) | 3.69 | 0.00104515 |
| microsomal glutathione S-transferase 1 | 3.67 | 0.041701 |
| arylacetamide deacetylase-like 1 | 3.67 | 0.000902645 |
| SPC25, NDC80 kinetochore complex component, homolog (S. ce | 3.65 | 0.00568662 |
| integrin, alpha 4 (antigen CD49D, alpha 4 subunit of VLA-4 | 3.62 | 0.0158411 |
| catenin (cadherin-associated protein), alpha-like 1 | 3.57 | 7.46E−05 |
| discs, large homolog 7 (Drosophila) | 3.56 | 0.0317074 |
| v-myb myeloblastosis viral oncogene homolog (avian)-lik | 3.55 | 0.0043878 |
| serglycin | 3.54 | 0.0443487 |
| centromere protein N | 3.53 | 0.000540143 |
| cyclin A2 | 3.53 | 0.00965934 |
| heat shock 22 kDa protein 8 | 3.52 | 0.0219583 |
| sema domain, immunoglobulin domain (Ig), short basic doma | 3.49 | 0.008548 |
| Rho GTPase activating protein 11A | 3.49 | 0.00834174 |
| Fanconi anemia, complementation group I | 3.43 | 0.00464532 |
| BUB1 budding uninhibited by benzimidazoles 1 homolog (yeast | 3.42 | 0.0108258 |
| ovary-specific acidic protein | 3.42 | 0.00334641 |
| cholinergic receptor, muscarinic 2 | 3.41 | 0.0320078 |
| cell division cycle 2, G1 to S and G2 to M | 3.41 | 0.0017111 |
| protein regulator of cytokinesis 1 | 3.39 | 0.0325664 |
| minichromosome maintenance complex component 5 | 3.38 | 0.00475504 |
| sperm associated antigen 5 | 3.37 | 0.00906321 |
| maternal embryonic leucine zipper kinase | 3.34 | 0.00908391 |
| small nucleolar RNA, C | 3.33 | 0.0298703 |
| carnitine palmitoyltransferase 1A (liver) | 3.33 | 0.00170894 |
| similar to Ubiquitin-conjugating enzyme E2S (Ubiqui | 3.33 | 0.000415822 |
| kinesin family member 11 | 3.33 | 0.00915145 |
| NIMA (never in mitosis gene a)-related kinase 7 | 3.33 | 0.00159114 |
| ADAM metallopeptidase with thrombospondin type 1 motif, | 3.32 | 0.0102751 |
| transforming, acidic coiled-coil containing protein 3 | 3.31 | 0.0014577 |
| cyclin B1 | 3.29 | 0.0103092 |
| MAD2 mitotic arrest deficient-like 1 (yeast) | 3.28 | 0.00488102 |
| dihydrofolate reductase | 3.28 | 0.00178879 |
| NIPA-like domain containing 3 | 3.27 | 0.00164708 |
| cell division cycle associated 2 | 3.26 | 0.0122226 |
| apolipoprotein B mRNA editing enzyme, catalytic polypep | 3.26 | 0.00308692 |
| cyclin B2 | 3.25 | 0.016544 |
| endonuclease domain containing 1 | 3.24 | 0.000429245 |
| dihydrofolate reductase pseudogene | 3.23 | 0.00141306 |
| ATPase, Na+ | 3.23 | 0.000381464 |
| replication factor C (activator 1) 3, 38 kDa | 3.23 | 0.00109668 |
| WD repeat domain 76 | 3.22 | 0.0023531 |
| pleckstrin 2 | 3.17 | 0.0304429 |
| Rac GTPase activating protein 1 | 3.17 | 0.00381613 |
| PHD finger protein 19 | 3.17 | 0.000177604 |
| deleted in lymphocytic leukemia, 2 | 3.15 | 0.0109528 |
| centromere protein I | 3.15 | 0.0106816 |
| BRCA1 associated RING domain 1 | 3.14 | 0.000540414 |
| regulator of G-protein signalling 4 | 3.13 | 0.00781061 |
| STAM binding protein-like 1 | 3.11 | 0.0181743 |
| sulfiredoxin 1 homolog (S. cerevisiae) | 3.10 | 5.14E−05 |
| chromosome 15 open reading frame 23 | 3.08 | 0.000147331 |
| TTK protein kinase | 3.08 | 0.0112171 |
| non-SMC condensin II complex, subunit G2 | 3.08 | 0.0130322 |
| villin 2 (ezrin) | 3.07 | 0.0131934 |
| stomatin | 3.06 | 0.00387095 |

TABLE 2-continued

Gene expression in Plurix cells (WO/2007/108003) compared to Celligen cells (teachings of the present invention)

| Gene | Celligen vs Plurix (fold change) | p-value (treat) |
|---|---|---|
| protein tyrosine phosphatase-like A domain containing | 3.06 | 0.0419644 |
| serpin peptidase inhibitor, clade B (ovalbumin), member | 3.05 | 0.0030439 |
| kinesin family member 4A | 3.05 | 0.0114203 |
| hypothetical protein DKFZp762E1312 | 3.05 | 0.00726778 |
| ubiquitin-conjugating enzyme E2S | 3.04 | 0.00118205 |
| hydroxysteroid dehydrogenase like 2 | 3.03 | 3.71E−05 |
| ATPase family, AAA domain containing 2 | 3.01 | 0.00415258 |
| TPX2, microtubule-associated, homolog (Xenopus laevis) | 3.00 | 0.0253137 |
| histone cluster 1, H4d | 3.00 | 0.030183 |
| kinesin family member 23 | 2.99 | 0.00790585 |
| heat shock 70 kDa protein 2 | 2.99 | 0.0215102 |
| origin recognition complex, subunit 1-like (yeast) | 2.99 | 0.00207753 |
| dihydrofolate reductase | 2.98 | 0.00307793 |
| hyaluronan-mediated motility receptor (RHAMM) | 2.97 | 0.00467816 |
| 3'-phosphoadenosine 5'-phosphosulfate synthase 2 | 2.97 | 1.43E−05 |
| glycerol-3-phosphate dehydrogenase 2 (mitochondrial) | 2.95 | 0.00211969 |
| nucleolar and spindle associated protein 1 | 2.95 | 0.00520875 |
| diaphanous homolog 3 (Drosophila) | 2.95 | 0.00107709 |
| kinesin family member 14 | 2.94 | 0.00947901 |
| histone cluster 1, H1b | 2.93 | 0.0470898 |
| guanine nucleotide binding protein (G protein), alpha inhi | 2.92 | 0.00184597 |
| minichromosome maintenance complex component 8 | 2.92 | 0.000841489 |
| cancer susceptibility candidate 5 | 2.92 | 0.0330594 |
| leukotriene B4 12-hydroxydehydrogenase | 2.92 | 0.000685452 |
| glutamate-cysteine ligase, modifier subunit | 2.91 | 0.00378868 |
| forkhead box M1 | 2.91 | 0.0203154 |
| adipose differentiation-related protein | 2.90 | 0.000331751 |
| membrane bound O-acyltransferase domain containing 1 | 2.90 | 0.01185 |
| ubiquitin-conjugating enzyme E2T (putative) | 2.90 | 0.00741886 |
| cell division cycle associated 3 | 2.89 | 0.006289 |
| integrin, alpha 3 (antigen CD49C, alpha 3 subunit of VLA-3 | 2.88 | 0.00574148 |
| coagulation factor XIII, B polypeptide | 2.88 | 0.0294465 |
| RAD51 homolog (RecA homolog, E. coli) (S. cerevisiae) | 2.87 | 0.000854739 |
| ATP-binding cassette, sub-family C (CFTR | 2.87 | 0.00382491 |
| family with sequence similarity 29, member A | 2.85 | 0.00111165 |
| SH2 domain containing 4A | 2.84 | 0.0323646 |
| membrane protein, palmitoylated 1, 55 kDa | 2.84 | 0.000396285 |
| CDC28 protein kinase regulatory subunit 1B | 2.84 | 0.0107391 |
| PSMC3 interacting protein | 2.84 | 0.00766442 |
| elastin microfibril interfacer 2 | 2.84 | 0.0192072 |
| topoisomerase (DNA) II alpha 170 kDa | 2.83 | 0.0321109 |
| transmembrane protein 106C | 2.82 | 0.000214223 |
| histone cluster 1, H3b | 2.80 | 0.0304598 |
| chromosome 18 open reading frame 24 | 2.80 | 0.00347442 |
| epidermal growth factor receptor pathway substrate 8 | 2.79 | 0.0194949 |
| high-mobility group nucleosomal binding domain 2 | 2.78 | 0.0030536 |
| SCL | 2.78 | 0.00390288 |
| hect domain and RLD 4 | 2.78 | 0.00679184 |
| ASF1 anti-silencing function 1 homolog B (S. cerevisiae) | 2.77 | 0.00543408 |
| thyroid hormone receptor interactor 13 | 2.76 | 0.0118319 |
| cell division cycle associated 8 | 2.75 | 0.00619878 |
| kinesin family member C1 | 2.74 | 0.00821937 |
| high-mobility group nucleosomal binding domain 2 | 2.73 | 0.00384071 |
| ornithine decarboxylase 1 | 2.73 | 0.00144868 |
| v-myb myeloblastosis viral oncogene homolog (avian)-like 2 | 2.71 | 0.00989416 |
| KIT ligand | 2.70 | 0.00641955 |
| dual-specificity tyrosine-(Y)-phosphorylation regulated ki | 2.70 | 0.0234606 |
| intraflagellar transport 80 homolog (Chlamydomonas) | 2.70 | 0.0247286 |
| transmembrane protein 48 | 2.69 | 0.00458248 |
| EBNA1 binding protein 2 | 2.69 | 0.00296292 |
| ZW10 interactor | 2.69 | 1.88E−05 |
| exonuclease 1 | 2.68 | 0.00739393 |
| transketolase (Wernicke-Korsakoff syndrome) | 2.68 | 1.92E−05 |
| somatostatin receptor 1 | 2.68 | 0.0144901 |
| isocitrate dehydrogenase 3 (NAD+) alpha | 2.67 | 0.00297129 |
| cytoskeleton associated protein 2 | 2.67 | 0.0030499 |
| minichromosome maintenance complex component 4 | 2.67 | 0.00342054 |

TABLE 2-continued

Gene expression in Plurix cells (WO/2007/108003) compared to Celligen cells (teachings of the present invention)

| Gene | Celligen vs Plurix (fold change) | p-value (treat) |
|---|---|---|
| inhibitor of DNA binding 1, dominant negative helix-loop-hel | 2.66 | 0.036485 |
| CDC28 protein kinase regulatory subunit 1B | 2.66 | 0.0145263 |
| keratin 18 | 2.66 | 8.40E−05 |
| CD97 molecule | 2.66 | 0.00994045 |
| chromosome 6 open reading frame 173 | 2.64 | 0.00222408 |
| BTB (POZ) domain containing 3 | 2.62 | 0.0166824 |
| deafness, autosomal dominant 5 | 2.62 | 0.00235481 |
| KIAA0286 protein | 2.62 | 0.00130563 |
| Fanconi anemia, complementation group D2 | 2.61 | 0.0281405 |
| polo-like kinase 4 (*Drosophila*) | 2.60 | 0.00209633 |
| ribonucleotide reductase M1 polypeptide | 2.60 | 0.000170076 |
| malic enzyme 1, NADP(+)-dependent, cytosolic | 2.59 | 0.0435444 |
| non-SMC condensin I complex, subunit H | 2.59 | 0.0216752 |
| S100 calcium binding protein A3 | 2.58 | 0.0324075 |
| ubiquitin-conjugating enzyme E2L 3 | 2.57 | 0.00343347 |
| BUB1 budding uninhibited by benzimidazoles 1 homolog beta | 2.56 | 0.0166047 |
| glycerol kinase | 2.55 | 2.66E−05 |
| TAF9B RNA polymerase II, TATA box binding protein (TBP)-as | 2.54 | 0.0170365 |
| TAF9B RNA polymerase II, TATA box binding protein (TBP)-as | 2.54 | 0.0170365 |
| histone cluster 1, H2bg | 2.52 | 0.000180822 |
| high-mobility group box 2 | 2.52 | 0.0196872 |
| NIMA (never in mitosis gene a)-related kinase 2 | 2.50 | 0.00289469 |
| proline rich 11 | 2.50 | 0.0357125 |
| myopalladin | 2.49 | 0.0255088 |
| brix domain containing 1 | 2.49 | 0.00471977 |
| cell division cycle associated 5 | 2.49 | 0.01021 |
| fucosidase, alpha-L-2, plasma | 2.49 | 0.00540929 |
| cyclin-dependent kinase 2 | 2.49 | 0.00250724 |
| lamin B receptor | 2.49 | 0.000151784 |
| hypoxanthine phosphoribosyltransferase 1 (Lesch-Nyhan synd | 2.49 | 0.000634057 |
| tripartite motif-containing 25 | 2.47 | 0.0456344 |
| proteasome (prosome, macropain) subunit, beta type, 9 (lar | 2.46 | 0.0202595 |
| proteasome (prosome, macropain) subunit, beta type, 9 (lar | 2.46 | 0.0202595 |
| proteasome (prosome, macropain) subunit, beta type, 9 (lar | 2.46 | 0.0202595 |
| sphingomyelin synthase 2 | 2.46 | 0.0020701 |
| transmembrane protein 62 | 2.45 | 0.00761064 |
| glucose-6-phosphate dehydrogenase | 2.44 | 0.00278311 |
| PHD finger protein 1 | 2.44 | 0.010191 |
| retinoblastoma-like 1 (p107) | 2.44 | 0.00319946 |
| KIAA1524 | 2.43 | 0.0380678 |
| ST6 (alpha-N-acetyl-neuraminyl-2,3-beta-galactosyl-1, | 2.43 | 0.00830766 |
| cofilin 2 (muscle) | 2.43 | 0.0459235 |
| hypothetical protein LOC201725 | 2.42 | 0.000313319 |
| cell division cycle 25 homolog A (*S. pombe*) | 2.42 | 0.000341692 |
| breast cancer 1, early onset | 2.41 | 0.0180553 |
| transaldolase 1 | 2.41 | 0.00199537 |
| mRNA turnover 4 homolog (*S. cerevisiae*) | 2.41 | 0.00373104 |
| glucosaminyl (N-acetyl) transferase 1, core 2 (beta-1,6-N- | 2.41 | 0.0197148 |
| cysteine rich transmembrane BMP regulator 1 (chordin-like) | 2.41 | 0.0267286 |
| tissue factor pathway inhibitor (lipoprotein-associated | 2.40 | 0.0356227 |
| chromosome 16 open reading frame 59 | 2.40 | 0.00185191 |
| glycogenin 1 | 2.39 | 0.0224317 |
| transmembrane protein 154 | 2.39 | 0.0045589 |
| tubulointerstitial nephritis antigen-like 1 | 2.39 | 0.00510812 |
| CTP synthase | 2.38 | 8.80E−05 |
| phenylalanyl-tRNA synthetase, beta subunit | 2.38 | 0.000245973 |
| geminin, DNA replication inhibitor | 2.38 | 0.00167629 |
| lamin B1 | 2.37 | 0.0477748 |
| SPC24, NDC80 kinetochore complex component, homolog (S. ce | 2.36 | 0.00287227 |
| glutathione reductase | 2.36 | 0.00353875 |
| ribosomal protein L22-like 1 | 2.36 | 0.00335381 |
| fumarylacetoacetate hydrolase (fumarylacetoacetase) | 2.36 | 3.88E−05 |

TABLE 2-continued

Gene expression in Plurix cells (WO/2007/108003) compared to Celligen cells (teachings of the present invention)

| Gene | Celligen vs Plurix (fold change) | p-value (treat) |
|---|---|---|
| small nucleolar RNA, C | 2.35 | 0.0188991 |
| family with sequence similarity 64, member A | 2.35 | 0.0019785 |
| epithelial cell transforming sequence 2 oncogene | 2.35 | 0.000571152 |
| polymerase (DNA directed), epsilon 2 (p59 subunit) | 2.34 | 0.00479612 |
| glycerol kinase | 2.34 | 3.37E−06 |
| glutathione S-transferase M2 (muscle) | 2.33 | 0.0402076 |
| elongation factor, RNA polymerase II, 2 | 2.33 | 0.0130017 |
| thioredoxin | 2.33 | 0.009636 |
| polymerase (DNA directed), alpha 2 (70 kD subunit) | 2.32 | 0.0033903 |
| breast cancer 2, early onset | 2.32 | 0.00586847 |
| CDC45 cell division cycle 45-like (*S. cerevisiae*) | 2.32 | 0.00735977 |
| H2A histone family, member Z | 2.32 | 0.0129697 |
| transporter 1, ATP-binding cassette, sub-family B (MDR | 2.31 | 0.0164234 |
| transporter 1, ATP-binding cassette, sub-family B (MDR | 2.31 | 0.0164234 |
| transporter 1, ATP-binding cassette, sub-family B (MDR | 2.31 | 0.0164234 |
| nucleolar complex associated 3 homolog (*S. cerevisiae*) | 2.30 | 0.000373346 |
| ATPase, Ca++ transporting, plasma membrane 4 | 2.30 | 0.023011 |
| minichromosome maintenance complex component 7 | 2.30 | 0.0457691 |
| TIMELESS interacting protein | 2.29 | 0.00771062 |
| von Hippel-Lindau binding protein 1 | 2.28 | 0.00329061 |
| ras-related C3 botulinum toxin substrate 2 (rho family, sma | 2.28 | 0.0292466 |
| thymopoietin | 2.28 | 0.0223176 |
| peptidylprolyl isomerase F (cyclophilin F) | 2.28 | 0.00093846 |
| activated leukocyte cell adhesion molecule | 2.27 | 0.00242163 |
| polycomb group ring finger 5 | 2.27 | 0.000294142 |
| Ran GTPase activating protein 1 | 2.27 | 9.68E−05 |
| replication factor C (activator 1) 4, 37 kDa | 2.26 | 0.00164152 |
| tubulin, beta 2C | 2.26 | 0.000346744 |
| minichromosome maintenance complex component 10 | 2.26 | 0.0037925 |
| H2B histone family, member S | 2.25 | 0.000885505 |
| gamma-glutamyl hydrolase (conjugase, folylpolygammaglutamyl | 2.25 | 0.0195219 |
| transcription termination factor, RNA polymerase II | 2.25 | 0.000393489 |
| polymerase (DNA directed), delta 2, regulatory subunit 50k | 2.25 | 0.0123823 |
| transporter 1, ATP-binding cassette, sub-family B (MDR | 2.25 | 0.00859077 |
| transporter 1, ATP-binding cassette, sub-family B (MDR | 2.25 | 0.00859077 |
| transporter 1, ATP-binding cassette, sub-family B (MDR | 2.25 | 0.00859077 |
| histone cluster 1, H2bf | 2.25 | 0.0124279 |
| eukaryotic translation initiation factor 1A, X-linked | 2.24 | 0.00330183 |
| phosphoglucomutase 2 | 2.24 | 0.00818204 |
| peroxisomal D3,D2-enoyl-CoA isomerase | 2.24 | 0.00148722 |
| interferon-induced protein with tetratricopeptide repeats | 2.24 | 0.0177928 |
| G-2 and S-phase expressed 1 | 2.23 | 0.0241887 |
| minichromosome maintenance complex component 2 | 2.23 | 0.0021347 |
| family with sequence similarity 72, member A | 2.23 | 0.00143248 |
| RMI1, RecQ mediated genome instability 1, homolog (S. cerev | 2.23 | 0.00294705 |
| FLJ20105 protein | 2.23 | 0.0127979 |
| multiple coagulation factor deficiency 2 | 2.22 | 0.0116892 |
| phytoceramidase, alkaline | 2.22 | 0.0157729 |
| coiled-coil domain containing 68 | 2.22 | 0.00227586 |
| dedicator of cytokinesis 11 | 2.21 | 0.00697577 |
| platelet-derived growth factor alpha polypeptide | 2.21 | 0.00176418 |
| N-acylsphingosine amidohydrolase (non-lysosomal cerami | 2.20 | 0.00728536 |
| S-phase kinase-associated protein 2 (p45) | 2.20 | 0.00230153 |
| polymerase (RNA) III (DNA directed) polypeptide G (32 kD) | 2.20 | 0.0298794 |
| ADP-ribosylation factor-like 6 interacting protein 1 | 2.20 | 0.00139745 |
| histone cluster 1, H2bh | 2.19 | 0.0377748 |
| origin recognition complex, subunit 5-like (yeast) | 2.19 | 0.049697 |
| CDC28 protein kinase regulatory subunit 2 | 2.19 | 0.0128024 |
| histone cluster 1, H4c | 2.19 | 0.0112695 |
| hypothetical protein LOC729012 | 2.19 | 0.000446087 |
| DEAD (Asp-Glu-Ala-Asp) box polypeptide 39 | 2.19 | 0.000340561 |

TABLE 2-continued

Gene expression in Plurix cells (WO/2007/108003) compared to Celligen cells (teachings of the present invention)

| Gene | Celligen vs Plurix (fold change) | p-value (treat) |
|---|---|---|
| chromatin assembly factor 1, subunit B (p60) | 2.18 | 0.0119687 |
| MLF1 interacting protein | 2.18 | 0.0177203 |
| microtubule associated serine | 2.18 | 0.00536974 |
| MHC class I polypeptide-related sequence B | 2.18 | 0.0165406 |
| shugoshin-like 2 (S. pombe) | 2.18 | 0.000852557 |
| COP9 constitutive photomorphogenic homolog subunit 6 (Arab | 2.18 | 0.000793512 |
| methylenetetrahydrofolate dehydrogenase (NADP+ dependent) | 2.18 | 0.00119726 |
| chromosome 6 open reading frame 167 | 2.18 | 0.0011095 |
| pituitary tumor-transforming 1 | 2.17 | 0.0485166 |
| ribonuclease H2, subunit A | 2.17 | 0.00669936 |
| X-ray repair complementing defective repair in Chinese ham | 2.16 | 0.0369865 |
| membrane protein, palmitoylated 5 (MAGUK p55 subfamily memb | 2.16 | 0.00211873 |
| karyopherin alpha 2 (RAG cohort 1, importin alpha 1) | 2.16 | 0.000650645 |
| pleckstrin homology domain containing, family A (phosphoi | 2.15 | 0.0256434 |
| ribosomal protein L39-like | 2.15 | 0.00429384 |
| karyopherin alpha 2 (RAG cohort 1, importin alpha 1) | 2.15 | 0.000700649 |
| amyloid beta (A4) precursor protein-binding, family B, m | 2.15 | 0.00201004 |
| minichromosome maintenance complex component 3 | 2.14 | 0.0018389 |
| histone cluster 1, H2ai | 2.14 | 0.0129155 |
| chromosome 13 open reading frame 34 | 2.14 | 0.000702936 |
| RAD18 homolog (S. cerevisiae) | 2.14 | 0.0016685 |
| WD repeat and HMG-box DNA binding protein 1 | 2.13 | 0.0034833 |
| sulfide quinone reductase-like (yeast) | 2.13 | 0.0473641 |
| chromosome 16 open reading frame 63 | 2.12 | 0.000804179 |
| M-phase phosphoprotein 1 | 2.12 | 0.0271814 |
| minichromosome maintenance complex component 6 | 2.12 | 0.0161279 |
| homeobox A9 | 2.11 | 0.00520942 |
| fibroblast growth factor 9 (glia-activating factor) | 2.10 | 0.0475844 |
| cell division cycle 25 homolog C (S. pombe) | 2.10 | 0.0169914 |
| chromosome 9 open reading frame 64 | 2.10 | 0.0265979 |
| U2AF homology motif (UHM) kinase 1 | 2.09 | 0.0255167 |
| replication factor C (activator 1) 2, 40 kDa | 2.09 | 0.00768959 |
| hypothetical protein LOC440894 | 2.09 | 0.0103358 |
| small nuclear ribonucleoprotein D1 polypeptide 16 kDa | 2.09 | 0.0334665 |
| CSE1 chromosome segregation 1-like (yeast) | 2.09 | 0.0013662 |
| phosphatidylinositol glycan anchor biosynthesis, class W | 2.09 | 0.0151967 |
| centromere protein O | 2.09 | 0.00397056 |
| family with sequence similarity 20, member B | 2.09 | 0.00460031 |
| hypothetical protein FLJ40869 | 2.09 | 0.00444509 |
| guanine nucleotide binding protein (G protein), gamma 11 | 2.08 | 0.00140559 |
| calcyclin binding protein | 2.08 | 0.00524566 |
| ATP-binding cassette, sub-family E (OABP), member 1 | 2.08 | 0.00454751 |
| CD44 molecule (Indian blood group) | 2.08 | 0.000651436 |
| exosome component 8 | 2.08 | 0.00132017 |
| family with sequence similarity 102, member B | 2.08 | 0.025743 |
| histone cluster 2, H3d | 2.07 | 0.0102932 |
| family with sequence similarity 33, member A | 2.07 | 0.000318673 |
| Fanconi anemia, complementation group B | 2.07 | 0.000255109 |
| kinesin family member 22 | 2.07 | 0.0192406 |
| histone cluster 1, H2ai | 2.07 | 0.0161621 |
| vaccinia related kinase 1 | 2.06 | 0.0233182 |
| integrator complex subunit 7 | 2.06 | 0.000841371 |
| flap structure-specific endonuclease 1 | 2.06 | 0.006882 |
| hypothetical protein FLJ25416 | 2.06 | 0.000177531 |
| ecotropic viral integration site 2B | 2.06 | 0.0171408 |
| retinitis pigmentosa 2 (X-linked recessive) | 2.05 | 0.0264185 |
| centromere protein L | 2.05 | 0.000880856 |
| cofactor required for Sp1 transcriptional activation, subu | 2.04 | 0.00141809 |
| chromosome 20 open reading frame 121 | 2.04 | 0.0146323 |
| family with sequence similarity 72, member A | 2.04 | 0.00162905 |
| family with sequence similarity 72, member A | 2.04 | 0.00165234 |
| eukaryotic translation initiation factor 1A, X-linked | 2.04 | 0.00520549 |
| elongation factor, RNA polymerase II, 2 | 2.03 | 0.0458007 |
| ATPase, Na+ | 2.03 | 0.0189108 |
| histone cluster 1, H3a | 2.03 | 0.0244273 |

TABLE 2-continued

Gene expression in Plurix cells (WO/2007/108003) compared to Celligen cells (teachings of the present invention)

| Gene | Celligen vs Plurix (fold change) | p-value (treat) |
|---|---|---|
| brix domain containing 1 | 2.03 | 0.00981178 |
| sushi domain containing 1 | 2.03 | 0.0258164 |
| ectonucleoside triphosphate diphosphohydrolase 6 (putativ | 2.03 | 0.00423628 |
| fructosamine 3 kinase | 2.03 | 0.00470972 |
| Bloom syndrome | 2.02 | 0.0209259 |
| tubulin, alpha 1c | 2.01 | 0.00862586 |
| E2F transcription factor 2 | 2.01 | 0.0496479 |
| exosome component 2 | 2.01 | 0.00649147 |
| kinesin family member 22 | 2.01 | 0.0242075 |
| LTV1 homolog (S. cerevisiae) | 2.01 | 0.00812652 |
| dihydrolipoamide S-acetyltransferase (E2 component of pyruv | 2.01 | 0.00179011 |
| v-ral simian leukemia viral oncogene homolog B (ras related | 2.01 | 0.012225 |
| ring finger and WD repeat domain 3 | 2.01 | 0.0013797 |
| annexin A1 | 2.01 | 0.0173578 |
| elaC homolog 2 (E. coli) | 2.00 | 0.00266504 |
| aldehyde dehydrogenase 9 family, member A1 | 2.00 | 0.00911609 |
| tubulin, alpha 4a | 2.00 | 0.0435427 |
| nuclear pore complex interacting protein | −2.00 | 0.00111223 |
| oculomedin | −2.01 | 0.00778869 |
| similar to PI-3-kinase-related kinase SMG-1 | −2.01 | 0.0356628 |
| golgi autoantigen, golgin subfamily a-like pseudogene | −2.01 | 0.00770626 |
| spectrin repeat containing, nuclear envelope 1 | −2.01 | 0.00438469 |
| nuclear pore complex interacting protein | −2.01 | 0.00117582 |
| sushi, nidogen and EGF-like domains 1 | −2.01 | 0.00161129 |
| integrin, alpha V (vitronectin receptor, alpha polypeptide | −2.02 | 0.00252702 |
| cyclin-dependent kinase inhibitor 2B (p15, inhibits CDK4) | −2.04 | 0.0150268 |
| lysyl oxidase-like 4 | −2.04 | 0.0120148 |
| nuclear pore complex interacting protein | −2.04 | 0.000213956 |
| calcium | −2.04 | 0.00657494 |
| calsyntenin 3 | −2.04 | 0.00300887 |
| cell adhesion molecule 1 | −2.05 | 0.0261129 |
| solute carrier family 22 (organic cation transporter), | −2.05 | 0.0137275 |
| RUN and FYVE domain containing 3 | −2.05 | 0.00387265 |
| glucosidase, alpha; acid (Pompe disease, glycogen storage di | −2.05 | 0.000418401 |
| nuclear pore complex interacting protein | −2.05 | 0.00988632 |
| proline-rich nuclear receptor coactivator 1 | −2.06 | 0.0039587 |
| membrane metallo-endopeptidase | −2.06 | 0.0152684 |
| PHD finger protein 21A | −2.06 | 0.00980401 |
| Rho GTPase-activating protein | −2.06 | 0.00705186 |
| homeobox B6 | −2.06 | 0.00301714 |
| nuclear pore complex interacting protein | −2.07 | 0.00032839 |
| phospholipase A2 receptor 1, 180 kDa | −2.07 | 0.00069343 |
| nuclear pore complex interacting protein | −2.08 | 0.000352007 |
| slit homolog 3 (Drosophila) | −2.08 | 0.02844 |
| nuclear pore complex interacting protein | −2.09 | 0.000414309 |
| cyclin-dependent kinase 6 | −2.09 | 0.0456892 |
| dynamin 1 | −2.09 | 0.00139674 |
| jumonji, AT rich interactive domain 1B | −2.09 | 0.00861002 |
| calcium binding and coiled-coil domain 1 | −2.09 | 0.00370041 |
| insulin-like growth factor 1 receptor | −2.09 | 0.00114467 |
| nuclear pore complex interacting protein | −2.10 | 0.000377834 |
| CD82 molecule | −2.10 | 0.0175517 |
| bromodomain adjacent to zinc finger domain, 2B | −2.10 | 9.88E−05 |
| — | −2.10 | 0.00666187 |
| synaptotagmin XI | −2.11 | 0.0129428 |
| KIAA1546 | −2.11 | 0.000255634 |
| jun B proto-oncogene | −2.12 | 0.0120169 |
| CXXC finger 6 | −2.12 | 0.0277527 |
| nuclear pore complex interacting protein | −2.14 | 0.00282604 |
| Cdon homolog (mouse) | −2.15 | 0.0350357 |
| B-cell CLL | −2.15 | 0.00343507 |
| nuclear pore complex interacting protein | −2.15 | 0.00263888 |
| v-abl Abelson murine leukemia viral oncogene homolog 1 | −2.16 | 0.0136688 |
| nuclear pore complex interacting protein | −2.16 | 0.00583397 |
| FAT tumor suppressor homolog 1 (Drosophila) | −2.18 | 0.0158766 |
| transformer-2 alpha | −2.18 | 0.012256 |
| chimerin (chimaerin) 1 | −2.18 | 0.0287031 |

TABLE 2-continued

Gene expression in Plurix cells (WO/2007/108003) compared to Celligen cells (teachings of the present invention)

| Gene | Celligen vs Plurix (fold change) | p-value (treat) |
|---|---|---|
| milk fat globule-EGF factor 8 protein | −2.18 | 0.000987073 |
| vitamin D (1,25-dihydroxyvitamin D3) receptor | −2.19 | 0.000192208 |
| neuroblastoma, suppression of tumorigenicity 1 | −2.20 | 0.00090639 |
| jumonji domain containing 1A | −2.20 | 0.0188513 |
| WNK lysine deficient protein kinase 1 | −2.21 | 1.57E−05 |
| protocadherin beta 14 | −2.21 | 0.0103892 |
| cortactin binding protein 2 | −2.21 | 2.28E−05 |
| WW domain containing transcription regulator 1 | −2.22 | 0.0379899 |
| cyclin L1 | −2.22 | 0.00831474 |
| nuclear factor of activated T-cells, cytoplasmic, calcine | −2.22 | 0.00786451 |
| pellino homolog 1 (Drosophila) | −2.23 | 0.00939357 |
| golgi autoantigen, golgin subfamily a-like pseudogene | −2.24 | 0.00603583 |
| chromosome 7 open reading frame 10 | −2.26 | 0.00738442 |
| golgi autoantigen, golgin subfamily a-like pseudogene | −2.27 | 0.00320764 |
| small Cajal body-specific RNA 17 | −2.27 | 0.0301336 |
| latent transforming growth factor beta binding protein 2 | −2.29 | 4.08E−05 |
| golgi autoantigen, golgin subfamily a, 8A | −2.29 | 0.0111179 |
| inhibin, beta A (activin A, activin AB alpha polypeptide) | −2.29 | 0.00877271 |
| solute carrier family 41, member 2 | −2.30 | 0.00453672 |
| forkhead box P1 | −2.30 | 0.0463138 |
| matrix metallopeptidase 14 (membrane-inserted) | −2.31 | 1.93E−05 |
| transcription factor 4 | −2.31 | 0.0367869 |
| jun oncogene | −2.32 | 7.21E−05 |
| neuroepithelial cell transforming gene 1 | −2.33 | 0.0109689 |
| asporin | −2.33 | 0.000659873 |
| v-fos FBJ murine osteosarcoma viral oncogene homolog | −2.35 | 0.0138624 |
| ephrin-B2 | −2.36 | 0.00611474 |
| WD repeat and SOCS box-containing 1 | −2.36 | 0.0387851 |
| similar to dJ402H5.2 (novel protein similar to wo | −2.36 | 0.00621503 |
| PX domain containing serine | −2.38 | 0.000927628 |
| collagen, type VII, alpha 1 (epidermolysis bullosa, dystr | −2.38 | 0.00109233 |
| AE binding protein 1 | −2.39 | 0.000105628 |
| peroxidasin homolog (Drosophila) | −2.40 | 0.00219049 |
| calcium channel, voltage-dependent, L type, alpha 1C sub | −2.41 | 0.0189661 |
| Prader-Willi syndrome chromosome region 1 | −2.45 | 0.0415526 |
| midline 1 (Opitz | −2.45 | 0.00130803 |
| nuclear pore complex interacting protein | −2.45 | 0.00354416 |
| chromosome 1 open reading frame 54 | −2.47 | 0.0186089 |
| transmembrane protein 16A | −2.48 | 0.0481085 |
| basic helix-loop-helix domain containing, class B, 2 | −2.49 | 0.00270257 |
| nuclear pore complex interacting protein | −2.50 | 0.00316496 |
| runt-related transcription factor 1 (acute myeloid leukemi | −2.50 | 0.000607387 |
| zinc finger protein 292 | −2.50 | 0.029832 |
| fibronectin leucine rich transmembrane protein 2 | −2.51 | 0.0135122 |
| nuclear pore complex interacting protein | −2.51 | 0.00283418 |
| potassium voltage-gated channel, subfamily G, member 1 | −2.54 | 0.0244306 |
| interleukin 19 | −2.54 | 0.0310328 |
| transforming growth factor, beta 3 | −2.54 | 0.0287865 |
| dihydropyrimidinase-like 3 | −2.55 | 0.0165203 |
| golgi autoantigen, golgin subfamily a, 8B | −2.56 | 0.0121417 |
| hypothetical protein PRO2012 | −2.57 | 0.00756704 |
| SATB homeobox 2 | −2.57 | 0.039781 |
| t-complex 11 (mouse)-like 2 | −2.57 | 0.0324227 |
| ring finger protein 122 | −2.57 | 0.0236621 |
| chromosome 8 open reading frame 57 | −2.59 | 0.00261522 |
| ADAM metallopeptidase with thrombospondin type 1 motif, | −2.60 | 0.0113968 |
| sushi, von Willebrand factor type A, EGF and pentraxin dom | −2.63 | 2.23E−05 |
| ST6 beta-galactosamide alpha-2,6-sialyltranferase 2 | −2.64 | 0.0216987 |
| sortilin-related VPS10 domain containing receptor 2 | −2.65 | 0.00936311 |
| protocadherin beta 9 | −2.66 | 0.0285124 |
| chromosome 5 open reading frame 13 | −2.67 | 0.00410172 |
| Enah | −2.68 | 0.0077547 |
| pyridoxal-dependent decarboxylase domain containing 2 | −2.69 | 0.00683647 |
| similar to nuclear pore complex interacting protein | −2.70 | 0.0187322 |
| nuclear pore complex interacting protein | −2.70 | 0.00368967 |

TABLE 2-continued

Gene expression in Plurix cells (WO/2007/108003) compared to Celligen cells (teachings of the present invention)

| Gene | Celligen vs Plurix (fold change) | p-value (treat) |
|---|---|---|
| transmembrane protein 119 | −2.70 | 0.00801387 |
| chromosome 14 open reading frame 37 | −2.70 | 0.0182453 |
| sushi-repeat-containing protein, X-linked 2 | −2.71 | 0.0253856 |
| PDZ domain containing RING finger 3 | −2.71 | 0.00931014 |
| collagen, type XII, alpha 1 | −2.72 | 0.000204664 |
| matrix-remodelling associated 5 | −2.72 | 0.000317637 |
| collagen, type V, alpha 1 | −2.72 | 0.0166427 |
| dystrophin related protein 2 | −2.72 | 0.0137557 |
| ATP-binding cassette, sub-family A (ABC1), member 1 | −2.73 | 0.00131361 |
| trophinin | −2.77 | 0.00298044 |
| cornichon homolog 3 (*Drosophila*) | −2.78 | 0.0261738 |
| formin binding protein 1-like | −2.78 | 0.00290401 |
| brain and acute leukemia, cytoplasmic | −2.78 | 0.0476919 |
| protein tyrosine phosphatase, receptor type, U | −2.80 | 0.0270428 |
| hypothetical protein MGC24103 | −2.82 | 0.0346673 |
| interferon induced with helicase C domain 1 | −2.83 | 0.0024839 |
| phospholipid transfer protein | −2.84 | 0.00999206 |
| immediate early response 3 | −2.87 | 0.0152127 |
| immediate early response 3 | −2.87 | 0.0152127 |
| ADAM metallopeptidase domain 12 (meltrin alpha) | −2.87 | 0.000870288 |
| synaptic vesicle glycoprotein 2A | −2.88 | 0.00704212 |
| chromosome 9 open reading frame 3 | −2.88 | 0.00410177 |
| thioredoxin interacting protein | −2.90 | 0.0135494 |
| early growth response 1 | −2.93 | 0.000425035 |
| small nucleolar RNA, C | −2.94 | 0.00666866 |
| small nucleolar RNA, C | −2.95 | 0.00765575 |
| immediate early response 3 | −2.99 | 0.0167309 |
| low density lipoprotein-related protein 1 (alpha-2-macroglo | −2.99 | 4.26E−05 |
| bicaudal C homolog 1 (*Drosophila*) | −2.99 | 0.0347162 |
| homeobox B2 | −3.03 | 0.00665994 |
| small nucleolar RNA, C | −3.10 | 0.0274043 |
| small nucleolar RNA, C | −3.10 | 0.0274043 |
| matrix metallopeptidase 2 (gelatinase A, 72 kDa gelatinase, | −3.13 | 5.59E−05 |
| KIAA1641 | −3.14 | 0.00659194 |
| collagen, type VI, alpha 3 | −3.14 | 2.09E−06 |
| homeobox A2 | −3.15 | 0.0435423 |
| SH3 and PX domains 2B | −3.15 | 0.0244357 |
| collagen, type VI, alpha 2 | −3.16 | 0.0149554 |
| chromosome 9 open reading frame 3 | −3.21 | 0.0233723 |
| small nucleolar RNA, C | −3.24 | 0.0104491 |
| small nucleolar RNA, C | −3.24 | 0.0104491 |
| — | −3.27 | 0.00488845 |
| UDP-N-acetyl-alpha-D-galactosamine:polypeptide N-acetylga | −3.35 | 0.00964109 |
| cholesterol 25-hydroxylase | −3.38 | 0.0445558 |
| KIAA1641 | −3.40 | 0.013175 |
| ring finger protein 144 | −3.40 | 0.0135334 |
| versican | −3.41 | 0.023885 |
| angiopoietin-like 2 | −3.42 | 0.0245161 |
| KIAA1641 | −3.44 | 0.0170531 |
| FBJ murine osteosarcoma viral oncogene homolog B | −3.54 | 0.00025573 |
| similar to RIKEN cDNA 1110018M03 | −3.59 | 0.00516476 |
| early growth response 2 (Krox-20 homolog, *Drosophila*) | −3.62 | 0.00821813 |
| dachsous 1 (*Drosophila*) | −3.63 | 0.00697244 |
| kinesin family member 26B | −3.64 | 0.00363199 |
| distal-less homeobox 5 | −3.66 | 0.000640157 |
| similar to Protein KIAA0220 | −3.69 | 0.0302619 |
| insulin-like growth factor 1 receptor | −3.71 | 3.42E−05 |
| protein tyrosine phosphatase, receptor type, N | −3.77 | 0.0294569 |
| KIAA1641 | −3.85 | 0.0191782 |
| sushi-repeat-containing protein, X-linked | −3.85 | 0.00370941 |
| microfibrillar-associated protein 2 | −3.91 | 0.0152167 |
| complement component 1, s subcomponent | −3.97 | 0.0395863 |
| CD24 molecule | −3.99 | 0.0340122 |
| homeobox B3 | −4.02 | 0.0354368 |
| trichorhinophalangeal syndrome I | −4.02 | 0.00557712 |
| Kallmann syndrome 1 sequence | −4.04 | 0.000548703 |
| leucine rich repeat containing 17 | −4.09 | 0.0263961 |
| plexin domain containing 2 | −4.32 | 0.031799 |
| PTK7 protein tyrosine kinase 7 | −4.42 | 0.000116114 |
| supervillin | −4.43 | 0.0412717 |

TABLE 2-continued

Gene expression in Plurix cells (WO/2007/108003) compared to
Celligen cells (teachings of the present invention)

| Gene | Celligen vs Plurix (fold change) | p-value (treat) |
|---|---|---|
| zinc finger protein 521 | −4.58 | 0.00668815 |
| calbindin 2, 29 kDa (calretinin) | −4.77 | 0.0290743 |
| ras homolog gene family, member J | −4.79 | 0.00197982 |
| integrin, alpha 11 | −4.80 | 0.000390317 |
| odz, odd Oz | −5.05 | 0.00172671 |
| F-box protein 32 | −5.52 | 0.0212957 |
| raftlin family member 2 | −5.72 | 0.0260454 |
| clusterin | −5.74 | 0.0303973 |
| neurotrimin | −5.79 | 3.78E−06 |
| WNT1 inducible signaling pathway protein 1 | −5.86 | 0.000672342 |
| insulin-like growth factor binding protein 5 | −6.34 | 0.011614 |
| sulfatase 2 | −6.34 | 5.88E−05 |
| microfibrillar-associated protein 4 | −6.93 | 0.00155578 |
| junctional adhesion molecule 2 | −7.07 | 0.0306758 |
| fibronectin type III domain containing 1 | −7.29 | 0.0334696 |
| sarcoglycan, delta (35 kDa dystrophin-associated glycoprotei | −7.37 | 0.000881984 |
| hephaestin | −7.53 | 0.0123141 |
| serpin peptidase inhibitor, clade F (alpha-2 antiplasmi | −7.66 | 0.00362941 |
| cystatin SN | −7.96 | 0.0496433 |
| hemicentin 1 | −8.18 | 0.0461603 |
| tenascin C (hexabrachion) | −8.32 | 8.26E−05 |
| biglycan | −8.62 | 0.00161284 |
| transmembrane, prostate androgen induced RNA | −11.20 | 0.000100935 |
| carboxypeptidase E | −11.22 | 0.00738131 |

Expression of cellular markers on PLX-C cells—the surface antigens expressed by PLX-C were examined using monoclonal antibodies. Results indicated that PLX-C cells were characterized by the positive markers: CD73, CD29 and CD105 and the negative markers: CD34, CD45, CD19, CD14, CD200 and HLA-DR. In some experiments, the immune phenotype test specifications were set as: ≧90% for all positive markers and ≦3% for all negative markers.

Figure 4D:
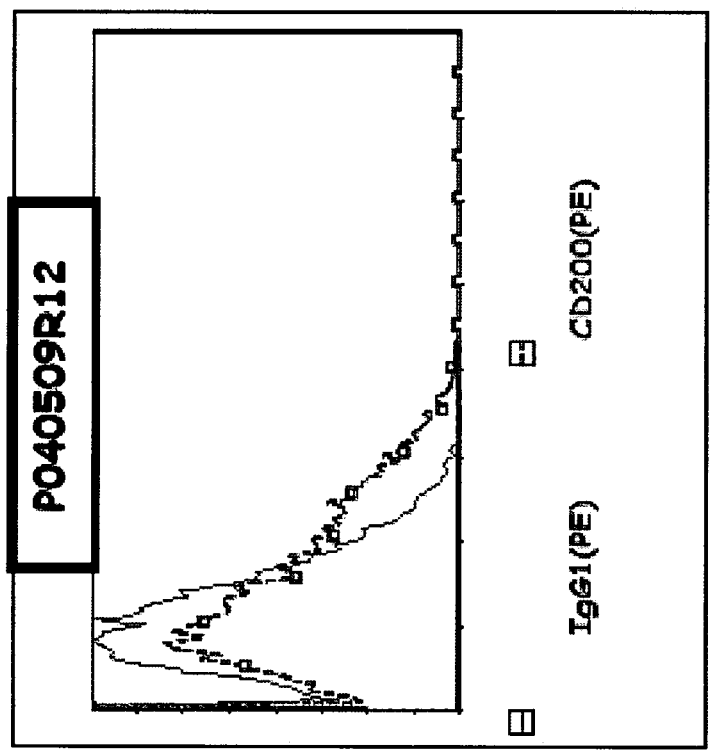

Furthermore, as shown in FIGS. 4A-B, PLX-C cultures did not express endothelial markers as shown by negative staining for the two endothelial markers CD31 and KDR. However, PLX-C expression of a fibroblast-typical marker was evident (expression of D7-fib, FIG. 4C). In addition, as is shown in FIG. 4D, PLX-C cells negatively express CD200.

Immunogenecity and immunomodulatory properties of PLX-C cells—as PLX-C is comprised of adherent cells derived from placenta, it is expected to express HLA type I, which is expressed by all cells of the body and is known to induce an alloreactive immune response. HLA type II and other co-stimulatory molecules are typically expressed only on the surface of Antigen Presenting Cells (APCs).

Figure 5A:
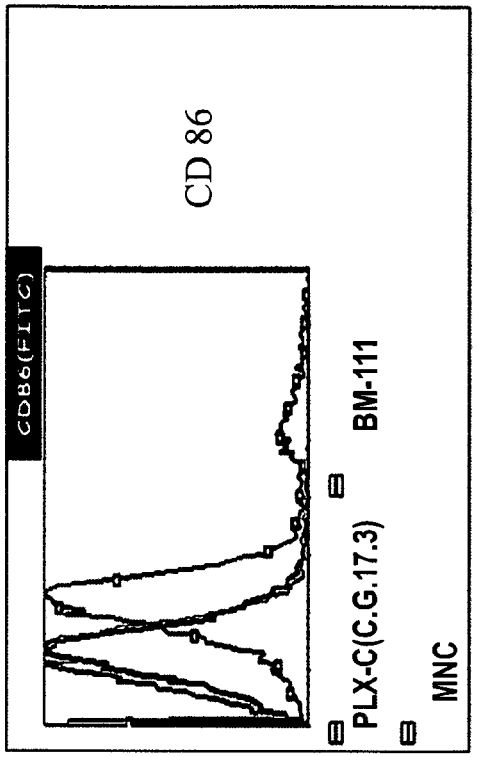
FIGS. 5A-D depict expression of stimulatory and co-stimulatory molecules on PLX-C cells.
Figure 5B:
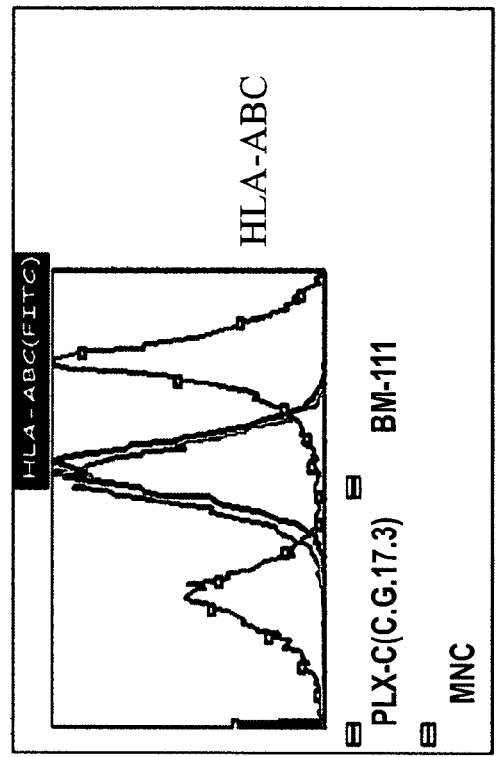
Figure 5C:
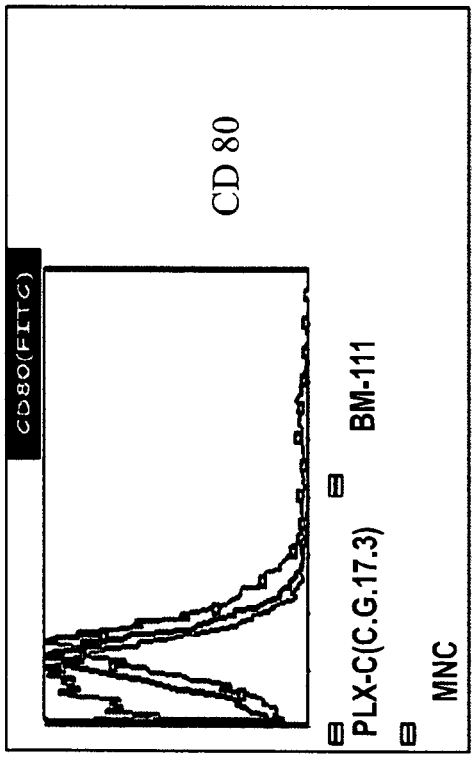
Figure 5D:
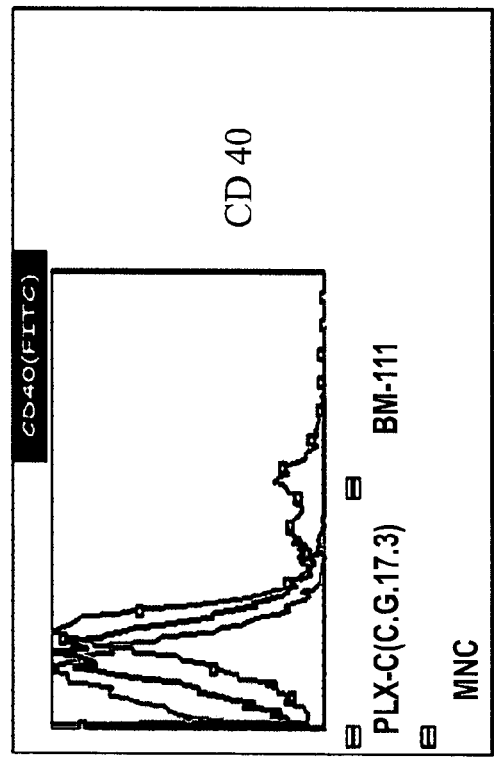

In order to examine the immunogenicity of the obtained PLX-C cells, the expression of co-stimulatory molecules on the surface of these cell membranes were performed. FACS analysis demonstrated the absence of CD80, CD86 and CD40 on the PLX-C cell membranes (FIGS. 5A-C). Moreover, PLX-C expressed low levels HLA class I as detected by staining for HLA A/B/C (FIG. 5D). The expression of stimulatory and co-stimulatory molecules was similar to bone marrow (BM) derived MSCs (as shown in FIGS. 5A-D).

Figures 6A, 6B:
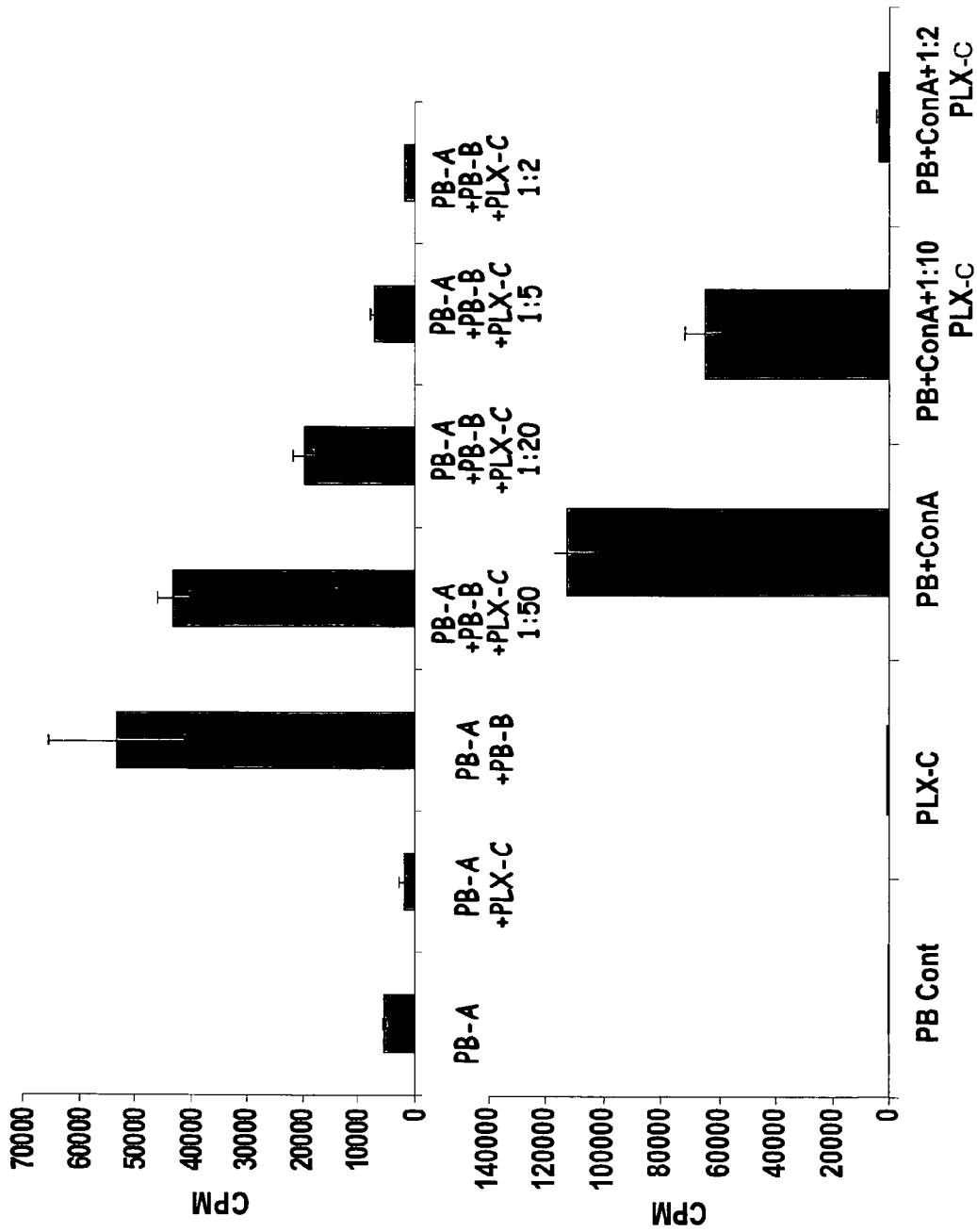
FIGS. 6A-B depict inhibition of lymphocyte proliferation by PLX-C.

To further investigate the immunogenicity as well as the immunomodulation properties of PLX-C cells, Mix Lymphocyte Reaction (MLR) tests were performed. As shown in FIG. 6A-B, PLX-C cells both escape allorecognition and reduce T cell response, as measured by Thymidine incorporation. Furthermore, the reduction in lymphocytes proliferation (evaluated by CPM measurement) was higher as the number of PLX-C cells increased (in a dose dependent manner). PLX-C also reduced lymphocyte proliferation following mitogenic stimuli, such as Concavalin A (Con A, FIG. 6B) and Phytohemagglutinin (PHA), and non-specific stimulation by anti-CD3, anti-CD28 (data not shown).

In order to investigate the mechanism of action by which PLX-C immunomodulate lymphocyte proliferation, and to see if this action is mediated via cell to cell interaction or cytokines secretion, PB derived Mononuclear cells (MNCs) were stimulated by PHA using the transwell method (which prevents cell to cell contact but enables the diffusion of cytokines between the two compartments). Results showed that the inhibition of proliferation maintained even when cell to cell contact was inhibited (data not shown).

Cytokines secretion—as depicted hereinabove, PLX-C reduce the proliferation rate of lymphocytes, probably through soluble factors. Further investigation of the cytokines secreted by lymphocytes in response to PLX-C was performed to elucidate the mechanism of action of PLX-C. As depicted in FIGS. 7A-B, culturing of mononuclear cells with PLX-C slightly reduces the secretion of the pro-inflammatory cytokine INFγ and dramatically reduces the secretion of TNFα (even in the presence of low amounts of PLX-C). In addition, following lipopolysaccharide (LPS) stimulation, PB derived MNCs secretion of IL-10 increased in the presence of PLX-C, while the secretion level of TNFα decreased, in a dose dependent manner (FIG. 7C).

Example 4

Comparison of Osteocyte Differentiation of 2D Adherent Cells of the Present Invention and Bone Marrow Cells The new adherent cells of the present invention (from placenta origin) were grown under osteocyte differentiation stimulating conditions at their 2D adherent cell stage in comparison to bone marrow derived cells.

Materials and Experimental Methods

Osteogenesis

Osteogenesis was carried out according to Chemicon osteogenesis kit (cat no. scr028, Millipore, MA, USA)

Osteogenesis Induction Medium

Osteogenesis induction medium was freshly made prior to each medium exchange using the kit components (See Table 3, below).

TABLE 3

Osteogenesis medium components

| Component | Stock concentration | Amount | Final con |
|---|---|---|---|
| DMEM low glucose (Invitrogen, Gibco) | | 8.7 ml | 87% |
| Serum (heat inactivated) | | 1 ml | 10% |
| dexamethasone | 1 mM | 1 μl | 0.1 μM |
| Asorbic Acid-2-Phosphate solution | 0.1M | 20 μl | 0.2 mM |
| Glycerol-2-Phosphate Solution | 1M | 100 μL | 10 Mm |
| L-glutamine | X 100 | 100 μl | X 1 |
| Pen & Strep | X 100 | 100 μl | X 1 |

To arrive at 1 mM dexamethasone solution, 900 μl ethanol was added to 100 μl dexamethasone 10 mM solution. Stock solution was stored with the rest of the kit's components at −20° C. A 50 ml serum vial was heat inactivated, divided into 5 ml aliquots and kept at −20° C. until use.

Coating 24-Well Tissue Culture Plates

A coating mixture comprising 12 μg/ml vitronectin and 12 μg/ml collagen (both included in the kit) was prepared by diluting each with 1×PBS.

The coating mixture was then added to the wells to cover the well surfaces (5 wells×2 plates were prepared). Plates were incubated overnight at room temperature. The coating mixture was then removed and the wells were rinsed once with PBS. Plates were aspirated right before use.

Cell Growth

Placenta derived cells (plc11-3-1) or bone marrow derived cells (BM108) were plated (200,000 cells per well) in 1 ml growth medium comprising DMEM (Invitrogen, Gibco), 10% FCS (Invitrogen, Gibco), 2 Mm L-glutamine (Sigma-Aldrich), 45 μg/ml Gentamicin-IKA (Teva Medical) and 0.25 μg/ml Fungizone (Invitrogen, Gibco). Placenta derived cells (4 wells×2 plates) or bone marrow derived cells (1 well×2 plates) were grown until 100% confluent (typically overnight) before initiating osteogenic differentiation.

When cells reached 100% confluence, growth medium was aspirated and replaced with 1 ml osteogenesis induction medium (differentiation day 1). Osteogenesis induction medium was replaced with fresh medium every 2-3 days for a total of 14-17 days.

As a control, one of the two plates (for each of the cell types) was not incubated with osteogenesis differentiation medium but rather with the growth medium (described hereinabove).

On day 17, osteocytes were fixed and stained with Alizarin Red Solution as depicted in detail below.

Staining Protocol

Osteocyte staining was performed by first carefully aspirating the medium from each well (carefully as to not aspirate the cells). Cells were then fixed by incubating in iced cold 70% ethanol for 1 hour at room temperature. The alcohol was then carefully aspirated and the cells were rinsed twice with water (5-10 minutes each wash). The water was then aspirated and alizarin red solution (500-1000 μl) was added to the cells.

Cells were incubated with alizarin red solution at room temperature for 30 minutes. Alizarin red was removed and the cells were washed 4 times with 1 ml water and aspirated after each wash. Finally, 1-1.5 ml water was added to each well to prevent cell drying. The plates were microscopically visualized by an inverted Nikon microscope.

Experimental Results

Osteocyte differentiation of placenta- or bone marrow-derived adherent cells in osteogenic induction medium resulted in differentiation of over 50% of the bone marrow cells, as demonstrated by positive alizarin red staining (FIG. 8B). On the contrary, none of the placental derived cells of the present invention showed any signs of osteogenic differentiation (see FIG. 8E and Table 4, below).

TABLE 4

Differentiation summary

| | BM 108 + BM109 | PLC-11-3-1 | PLC-8-2-1 | Plc-15-3-4-2 | Plc 4-3-1 |
|---|---|---|---|---|---|
| Osteocytes | +++ | − | − | − | − |
| Adipocytes | +++ | − | − | − | − |

Example 5

Comparison of Osteocyte Differentiation of 2D Adherent Cells of the Present Invention and Bone Marrow Cells in Modified Growth Medium The adherent cells of the present invention (from placenta origin, at their 2D adherent cell stage) or bone marrow derived cells were grown under osteocyte differentiation stimulating conditions in a modified osteogenic medium comprising Vitamin D and higher concentrations of dexamethasone.

Materials and Experimental Methods

Osteogenesis Induction Medium

Osteogenesis induction medium was freshly made prior to each medium exchange using the components listed in Table 5, below, along with Vitamin D.

TABLE 5

Osteogenesis medium components

| Component | Stock con | Amount | Final con |
|---|---|---|---|
| DMEM high glucose (Biological Industries, Bet Haemek, Israel) | | 8.7 ml | 87% |
| L-glutamine | X 100 | 100 μl | X 1 |
| Serum (heat inactivated) | | 1 ml | 10% |
| Dexamethasone (Chemicon) | 10 mM | 10 μl | 10 μM |
| Asorbic Acid-2-Phosphate solution (Chemicon) | 0.1M | 20 μl | 0.2 mM |
| Glycerol-2-Phosphate Solution (Chemicon) | 1M | 100 μL | 10 Mm |
| Vitamin D (Sigma) | 10 μM | 10 μL | 10 nM |
| Gentamycin (Biological Industries, Bet Haemek, Israel) | X 100 | 100 μl | X 1 |

A 50 ml serum vial was heat inactivated, divided into 5 ml aliquots and kept at −20° C. until use.

Coating 48-Well Tissue Culture Plates

A coating mixture comprising 12 μg/ml vitronectin and 12 μg/ml collagen (both from Chemicon) was prepared by diluting each with 1×PBS.

The coating mixture was then added to the wells to cover the well surfaces (5 wells×2 plates were prepared). Plates were incubated overnight at room temperature. The coating mixture was then removed and the wells were rinsed once with PBS. Plates were aspirated right before use.

Cell Growth

Placenta derived cells (PLC8-2-1, PLC 15 3-4-2 or PLC 19-4-3-1 fetal cells) were plated (100,000 cells per well) in 0.5 ml growth medium comprising DMEM (Invitrogen, Gibco), 10% FCS (Invitrogen, Gibco), 2 Mm L-glutamine (Sigma-Aldrich), 45 µg/ml Gentamicin-IKA (Teva Medical) and 0.25 µg/ml Fungizone (Invitrogen, Gibco) (4 wells×2 plates). Bone marrow derived cells (BM109) were plated (150,000 cells per well) in 0.5 ml growth medium (as described above) (1 well×2 plates). Cells were grown until 100% confluent (typically overnight) before initiating osteogenic differentiation.

When cells reached 100% confluence, growth medium was aspirated and replaced with 0.5 ml osteogenesis induction medium (differentiation day 1). Osteogenesis induction medium was replaced with fresh medium every 2-3 days for a total of 26 days.

As a control, one of the two plates (for each of the cell types) was not incubated with osteogenesis differentiation medium but rather with the growth medium (described hereinabove).

On day 26, osteocytes were fixed and stained with Alizarin Red Solution as depicted in detail below.

Staining Protocol

Osteocyte staining was performed by first carefully aspirating the medium from each well (carefully as to not aspirate the cells). Cells were then fixed by incubating in iced cold 70% ethanol for 1 hour at room temperature. The alcohol was then carefully aspirated and the cells were rinsed twice with water (5-10 minutes each wash). The water was then aspirated and alizarin red solution (500-1000 µl) was added to the cells. Cells were incubated with alizarin red solution at room temperature for 30 minutes. Alizarin red was removed and the cells were washed 4 times with 1 ml water and aspirated after each wash. Finally, 1-1.5 ml water was added to each well to prevent cell drying. The plates were microscopically visualized by an inverted Nikon microscope.

Experimental Results

Osteogenic differentiation of placenta- or bone marrow-derived adherent cells was performed by modification of the protocol described in Example 4, hereinabove, according to previous teachings [Parloni et al. (2008) Stem Cells 26(2): 300-11]. The main difference between the growth conditions presented in Example 4 and the results presented herein was the addition of vitamin D to the differentiation medium and the higher concentrations of dexamethasone. As evident from the results, over 50% of the bone marrow cells underwent differentiation into osteocytes, as demonstrated by positive alizarin red staining (see FIG. 9B). However, none of the placental derived cells of the present invention showed any signs of osteogenic differentiation (see FIG. 9E and Table 4, hereinabove).

Example 6

Comparison of Adipocyte Differentiation of 2D Adherent Cells of the Present Invention and Bone Marrow Cells The new adherent cells of the present invention (from placenta origin) were grown under adipocyte differentiation stimulating conditions at their 2D adherent cell stage in comparison to bone marrow derived cells.

Materials and Experimental Methods

Adipogenesis

Adipogenesis was carried out according to Chemicon adipogenesis kit (Chemicon adipogenesis kit, cat no. scr020, Millipore, MA, USA)

Adipogenesis Induction Medium

Adipogenesis induction or maintenance mediums were freshly prepared prior to every medium exchange using the components depicted in Tables 6 and 7, below.

TABLE 6

Adipogenesis induction medium components

| Component | Stock con | Amount | Final con |
| --- | --- | --- | --- |
| DMEM low glucose (Biological Industries, Bet Haemek, Israel) |  | 4.4 ml | 90% |
| Serum (heat inactivated) |  | 0.5 ml | 10% |
| Dexamethasone (Sigma) | 10 mM | 0.5 µl | 1 µM |
| IBMX (Sigma) | 0.5M | 5 µl | 0.5 mM |
| Insulin (Sigma) | 10 mg/ml | 5 µL | 10 µg/ml |
| Indomethacin (Sigma) | 10 mM | 50 µl | 100 µM |
| Pen & Strep | X 100 | 50 µl | X 1 |

TABLE 7

Adipogenesis maintenance medium components

| Component | Stock con | Amount | Final con |
| --- | --- | --- | --- |
| DMEM low glucose |  | 4.4 ml | 90% |
| Serum (heat inactivated) |  | 0.5 ml | 10% |
| Insulin | 10 mg/ml | 5 µL | 10 µg/ml |
| Pen & Strep | X 100 | 50 µl | X 1 |

Cell Growth

Placenta derived cells (plc11-3-1) or bone marrow derived cells (BM108) were plated (200,000 cells per well) in 1 ml growth medium comprising DMEM (Invitrogen, Gibco), 10% FCS (Invitrogen, Gibco), 2 Mm L-glutamine (Sigma-Aldrich), 45 µg/ml Gentamicin-IKA (Teva Medical) and 0.25 µg/ml Fungizone (Invitrogen, Gibco). Placenta derived cells (4 wells×2 plates) or bone marrow derived cells (1 well×2 plates) were grown until 100% confluent (typically overnight) before initiating adipogenesis differentiation.

When cells reached 100% confluence, growth medium was aspirated and replaced with 1 ml adipogenesis induction medium (differentiation day 1). Adipogenesis induction medium was replaced with fresh medium every 2-3 days for a total of 25 days (as depicted in detail in Table 8, hereinbelow). Of note, monolayers of adipogenic cells were extremely fragile and could easily dislodged from plates, therefore, medium changes were performed with gentle medium changes to avoid disruption of the lipid droplets.

As a control, one of the two plates (for each of the cell types) was not incubated with adipogenesis differentiation medium but rather with the growth medium (described hereinabove).

TABLE 8

Adipogenesis differentiation schedule

| Day | Medium |
| --- | --- |
| 1 | Adipogenesis Induction medium |
| 3 | Adipogenesis Induction medium |
| 5 | Adipogenesis Induction medium |
| 7 | Adipogenesis Maintenance medium |

TABLE 8-continued

Adipogenesis differentiation schedule

| Day | Medium |
|---|---|
| 9 | Adipogenesis Induction medium |
| 11 | Adipogenesis Induction medium |
| 13 | Adipogenesis Induction medium |
| 15 | Adipogenesis Maintenance medium |
| 17 | Adipogenesis Induction medium |
| 19 | Adipogenesis Induction medium |
| 21 | Adipogenesis Induction medium |

On day 25, adipocytes were fixed and stained with oil red solution as depicted in detail below.

Staining Protocol

Adipocyte staining was performed by first carefully aspirating the medium from each well (carefully as to not aspirate the cells). Cells were then fixed by incubating in 4% Para formaldehyde for 30-40 minutes at room temperature. The fixative was then carefully aspirated and the cells were rinsed three times with PBS (5-10 minutes each wash). Next, the PBS was aspirated and the cells were rinsed twice in water. The water was then aspirated and oil red solution (500-1000 µl) was added to the cells. Cells were incubated with oil red solution at room temperature for 50 minutes. Oil red solution was removed and the cells were washed 4 times with 1 ml water and aspirated after each wash. Finally, 1-1.5 ml water was added to each well to prevent cell drying. The plates were microscopically visualized by an inverted Nikon microscope.

Preparation of Oil Red Solution

Stock of 0.25 g oil red (Sigma) was used which was dissolved in 50 ml iso-propanol by incubating 10-15 min in 37° C. bath.

For use, 30 ml of the stock stain was mixed with 20 ml DDW (left to stand for 10 minutes and then filtered with coffee filter paper). The oil red solution was prepared fresh for each use.

Experimental Results

Adipocyte differentiation of placenta- or bone marrow-derived adherent cells in adipocyte induction medium resulted in differentiation of over 50% of the bone marrow derived cells (see FIG. 8C), as demonstrated by positive oil red staining and by typical morphological changes (e.g. accumulation of oil droplets in the cytoplasm). In contrast, none of the placental derived cells of the present invention differentiated into adipocytes (see FIG. 8F and Table 4, hereinabove).

Example 7

Comparison of Adipocyte Differentiation of 2D Adherent Cells of the Present Invention and Bone Marrow Cells in Modified Growth Medium The adherent cells of the present invention (from placenta origin, at their 2D adherent cell stage) or bone marrow cells were stimulated to differentiate into adipocytes in a modified adipocyte medium comprising a higher level of Indomethacine.

Materials and Experimental Methods

Adipogenesis Induction Medium

Adipogenesis induction medium was freshly prepared prior to every medium exchange using the components depicted in Table 9, below.

TABLE 9

Adipogenesis induction medium components

| Component | Stock con | Amount | Final con |
|---|---|---|---|
| DMEM low glucose | | 4.4 ml | 90% |
| Serum (heat inactivated) | | 0.5 ml | 10% |
| Dexamethasone (Sigma) | 1 mM | 5 µl | 1 µM |
| IBMX (Sigma) | 0.5M | 5 µl | 0.5 mM |
| Insulin (Sigma) | 10 mg/ml | 5 µL | 10 µg/ml |
| Indomethacin (Sigma) | 10 mM | 200 µl | 100 µM |
| Gentamycine (Biological Industries) | | 10 µl | |

Cell Growth

Placenta derived cells (PLC8-2-1, PLC 15 3-4-2 or PLC 19-4-3-1 fetal cells) were plated (100,000 cells per well) in 0.5 ml growth medium comprising DMEM (Invitrogen, Gibco), 10% FCS (Invitrogen, Gibco), 2 Mm L-glutamine (Sigma-Aldrich), 45 µg/ml Gentamicin-IKA (Teva Medical) and 0.25 µg/ml Fungizone (Invitrogen, Gibco) (5 wells×2 plates).

Bone marrow derived cells (BM109) were plated (100,000 cells per well) in 0.5 ml growth medium comprising DMEM (Invitrogen, Gibco), 10% FCS (Invitrogen, Gibco), 2 Mm L-glutamine (Sigma-Aldrich), 45 µg/ml Gentamicin-IKA (Teva Medical) and 0.25 µg/ml Fungizone (Invitrogen, Gibco) (4 well×2 plates). Cells were grown until 100% confluent (typically overnight) before initiating adipogenesis differentiation.

When cells reached 100% confluence, growth medium was aspirated and replaced with 0.5 ml adipogenesis induction medium (differentiation day 1). Adipogenesis induction medium was replaced with fresh medium every 2-3 days for a total of 3-4 weeks.

As a control, one of the two plates (for each of the cell types) was not incubated with adipogenesis differentiation medium but rather with the growth medium (described hereinabove).

On day 26, adipocytes were fixed and stained with oil red solution as depicted in detail below.

Staining Protocol

Adipocyte staining was performed by first carefully aspirating the medium from each well (carefully as to not aspirate the cells). Cells were then fixed by incubating in 4% Para formaldehyde for 30-40 minutes at room temperature. The fixative was then carefully aspirated and the cells were rinsed three times with PBS (5-10 minutes each wash). Next, the PBS was aspirated and the cells were rinsed twice in water. The water was then aspirated and oil red solution (500-1000 µl) was added to the cells. Cells were incubated with oil red solution at room temperature for 50 minutes. Oil red solution was removed and the cells were washed 3 times with 1 ml double distilled water and aspirated after each wash. Finally, 1-1.5 ml water was added to each well to prevent cell drying. The plates were microscopically visualized by an inverted Nikon microscope.

Preparation of Oil Red Solution

Stock of 0.25 g oil red (Sigma) was used which was dissolved in 50 ml iso-propanol by incubating 10-15 min in 37° C. bath.

For use, 30 ml of the stock stain was mixed with 20 ml DDW (left to stand for 10 minutes and then filtered with coffee filter paper). The oil red solution was prepared fresh for each use.

Experimental Results

Adipocyte differentiation of placenta- or bone marrow-derived adherent cells was performed by modification of the protocol in Example 6, hereinabove, according to previous teachings [Parloni et al. (2007), supra]. The main difference between the growth conditions presented in Example 6 and the results presented herein was the higher concentration of Indomethacine. As evident from the results, over 50% of the bone marrow derived cells underwent differentiation into adipocytes (see FIG. 9C), as demonstrated by positive oil red staining and by typical morphological changes (e.g. accumulation of oil droplets in the cytoplasm). In contrast, none of the placental derived cells of the present invention exhibited morphological changes typical of adipocytes (see FIG. 9F and Table 4, hereinabove).

Example 8

Biodistribution of PLX-C

Materials and Experimental Methods

Transfection of PLX-C Cells with Luciferase Expression Vector

Figure 10:
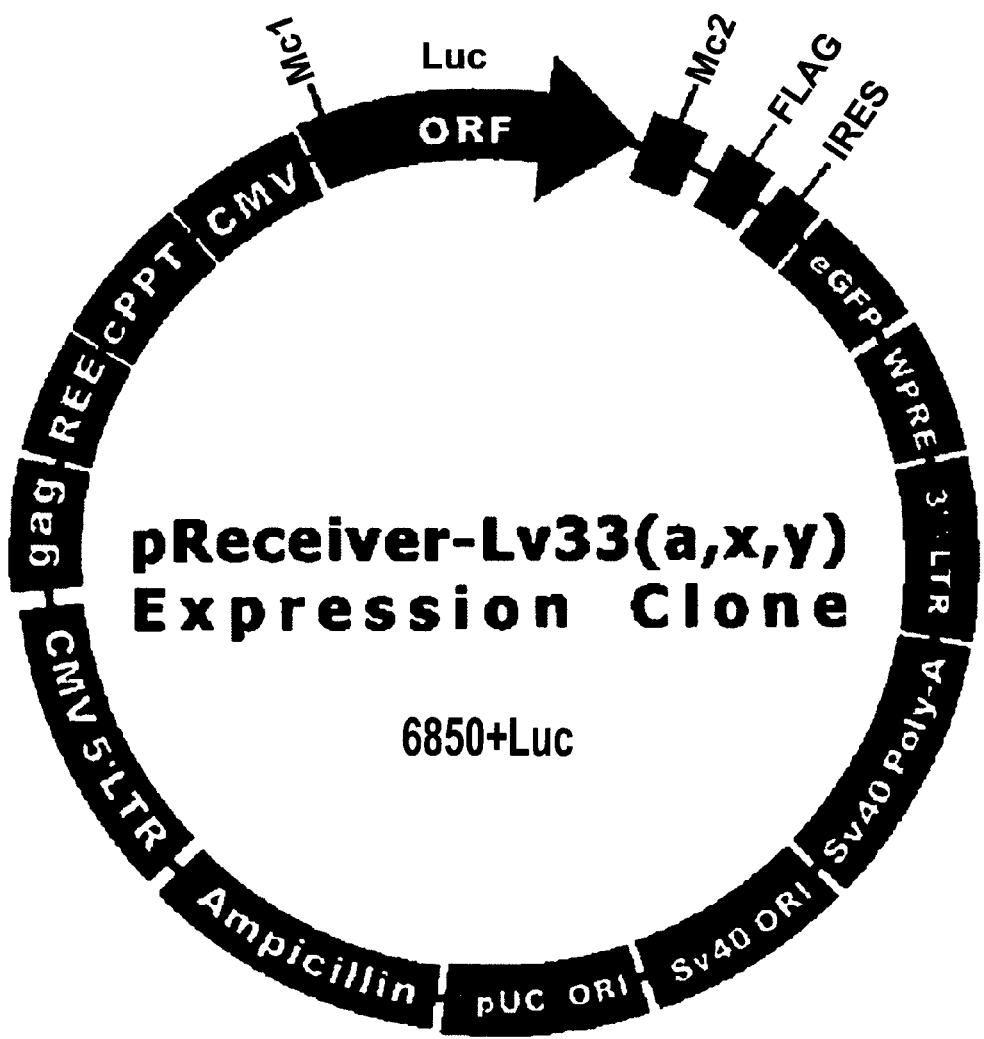
FIG. 10 depicts the Luciferase expression vector used to infect PLX-C cells. Expression vector Lv33 from OmicsLink was used herein. The Luciferase gene was cloned into the ORF.

PLX-C cells were stably infected with a lentiviral construct expressing the luciferase gene under the CMV promoter (FIG. 10).

Production of Infecting Virus

293TN producer cells were grown in DMEM medium (Gibco) supplemented with serum and antibiotics for 2-3 days (50-70% confluency) prior to transfection. A mixture of 10 μg of the packaging plasmid and 2 μg of expression construct and 20 μl of Plus™ Reagent (Invitrogen) were added to 400 μl of DMEM without supplements. The mixture was incubated for 15 min at room temperature (RT) and Lipofectamine™ (30 μl dilutes in 400 μl of DMEM were added). The mixture was incubated at RT for 15 min. 293TN cells were washed and transferred to 2% serum media and transfection mixture was added. Cells were incubated in CO2 incubator at 37° C. over night and medium was collected 24-60 hrs post infection. Peak virus production was achieved after 48 hrs. Medium was collected, and centrifuged at 3000 rpm at room temperature for 5 minutes to pellet cell debris. Following centrifugation, the supernatant was filtered through Millex-HV 0.45 μm PVDF filters (Millipore, Cat. #SLHVR25LS).

Infection of PLX-C

PLX-C cells were seeded in a 24-well plate at a density of $0.6-1 \times 10^5$ cells per well in complete medium 24 hours prior to viral infection. After 24 hrs, 0.5 ml of virus suspension (diluted in complete medium with Polybrene at a final concentration of 5-8 μg/ml) was added. Cells were incubated for 24 hrs, then medium was replaced by complete DMEM medium and cells were incubated at 37° C. with 5% CO2 overnight. At day 4, the culture reached confluency and was split by 1:3 to 1:5, cells were allowed to grow for 48 hours in complete DMEM then cells were analyzed for Luciferase expression.

Efficiency rates of infection were close to 100%. Evaluation of luminescence in living cells and in living mice was performed using the IVIS Lumina Imaging system, which included a highly sensitive CCD camera that captured the luciferase luminescence signal.

Two weeks post infection $2 \times 10^6$ cells were injected IM or IV into SCID/Beige, NOD/SCID, SCID and Balb/C mice. Injected cells were monitored using the described IVIS system.

Experimental Results

Figure 11:
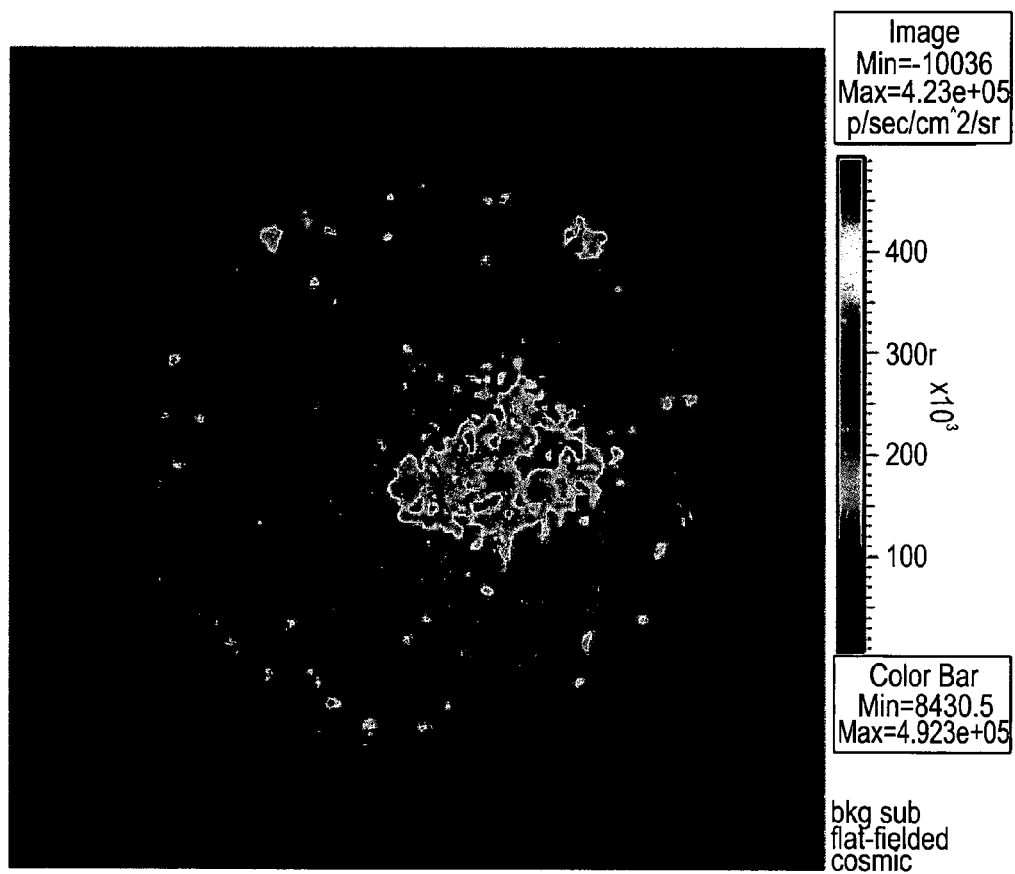
FIG. 11 depicts high Luciferase expression by infected PLX-C cells. Cells were infected with the Luciferase expression vector and visualized by the IVIS system 48 hours post infection. Of note, cells exhibited high levels of Luciferase expression.
Figure 12A:
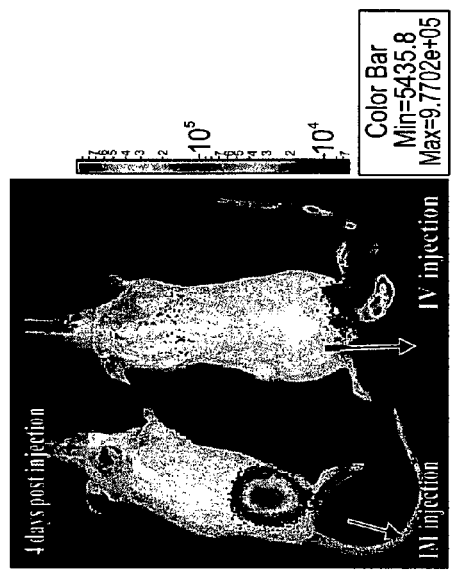
FIGS. 12A-D depict injection of 2×10$^6$ Luciferase expressing PLX-C cells into SCID/Beige mice. One mouse was injected IM and one IV. The injected mice were monitored using the IVIS system in order to asses the in vivo biodistribution of PLX-C. IVIS results of days 1 (FIG. 12A), day 4 (FIG. 12B), day 6 (FIG. 12C) and day 22 (FIG. 12D) are presented.
Figure 12B:
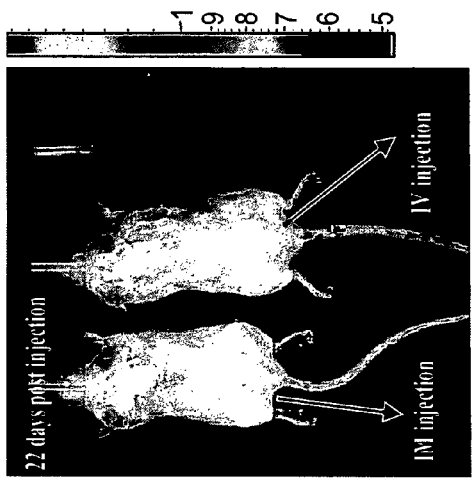
Figure 12C:
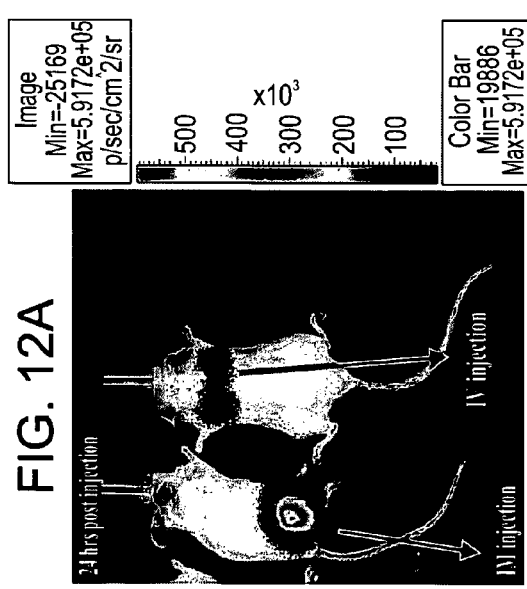
Figure 12D:
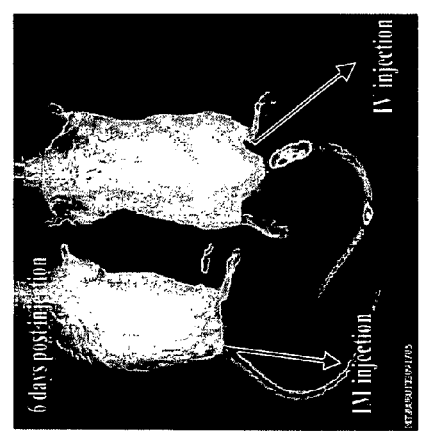

As evident from the results, PLX-C cells continued to divide following infection, and expression levels of Luciferase in the growing cells remained strong and stable (FIG. 11).

Once PLX-C cells were injected into Balb/C mice, the biodistribution pattern was examined. As evident from the results, cells disappeared 72 hrs post IM injection (data not shown). However, PLX-C cells retained constant high levels of Luciferase expression, in vitro, for over three weeks (data not shown).

As shown in FIGS. 12A-D, cells injected IM into SCID/Beige mice immunodeficient mice retained up to 5 days at the site of injection and were not observed thereafter. PLX-C cells injected IV into SCID/Beige mice migrated after 24 hrs to the lungs, then to the site of injection (presumably homing to site of injury). Afterwards cells disappear gradually and were not observed after 3-4 weeks. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of culturing adherent cells from a placenta or adipose tissue, the method comprising culturing the adherent cells from the placenta or adipose tissue under three-dimensional (3D) culturing conditions which allow cell expansion, said conditions comprising perfusion, wherein the rate of said perfusion is adjusted according to the glucose concentration of the culture medium, and wherein said culture medium is changed at a glucose concentration of about 500 mg/L to about 600 mg/L.

2. The method of claim 1, wherein said 3D culturing conditions:
   (a) comprise a 3D bioreactor; or
   (b) comprise an adherent material selected from the group consisting of glass. plastic, polyester, and polypropylene, polystyrene, dextran and collagen; or
   (c) are effected for at least 3 days; or
   (d) comprise a combination thereof.

3. The method of claim 1, wherein said culturing of said cells is effected until at least 10% of said cells are proliferating.

4. The method of claim 1, wherein said 3D culturing conditions comprise:
   (i) culturing said adherent cells in a bioreactor having a cylinder packed bed and the culture medium is flown through the packed bed; or
   (ii) culturing said adherent cells in a growth phase maintaining working volume of at least about 1,500 mL; or
   (iii) seeding said adherent cells at a seeding concentration of at least about $0.1 \times 10^6$ cell/ml; or
   (iv) culturing said adherent cells in a bioreactor having a carrier of at least 30 grams weight.

* * * * *